(12) United States Patent
Myers et al.

(10) Patent No.: US 11,373,554 B2
(45) Date of Patent: Jun. 28, 2022

(54) PELVIC MODEL FOR ROBOTIC, LAPAROSCOPIC, AND ABDOMINAL/OPEN APPROACH SURGICAL TRAINING

(71) Applicant: The Charlotte Mecklenburg Hospital Authority, Charlotte, NC (US)

(72) Inventors: Erinn M. Myers, Fort Mill, NC (US); Megan E. Tarr, Charlotte, NC (US); Brittany L. Anderson-Montoya, Charlotte, NC (US); Heather Fasano, Charlotte, NC (US); Smitha Vilasagar, Charlotte, NC (US)

(73) Assignee: The Charlotte Mecklenburg Hospital Authority, Charlotte, NC (US)

( * ) Notice: Subject to any disclaimer, the term of this patent is extended or adjusted under 35 U.S.C. 154(b) by 358 days.

(21) Appl. No.: 16/274,759

(22) Filed: Feb. 13, 2019

(65) Prior Publication Data
US 2019/0251870 A1    Aug. 15, 2019

Related U.S. Application Data

(60) Provisional application No. 62/630,442, filed on Feb. 14, 2018.

(51) Int. Cl.
| | | |
|---|---|---|
| *G09B 23/34* | (2006.01) | |
| *G09B 23/30* | (2006.01) | |
| *A61B 17/00* | (2006.01) | |
| *G09B 23/28* | (2006.01) | |
| *A61B 34/30* | (2016.01) | |

(Continued)

(52) U.S. Cl.
CPC ........... *G09B 23/303* (2013.01); *G09B 23/30* (2013.01); *G09B 23/34* (2013.01); *A61B 17/00234* (2013.01); *A61B 17/0483* (2013.01); *A61B 17/062* (2013.01); *A61B 17/42* (2013.01); *A61B 34/30* (2016.02); *A61B 2017/00716* (2013.01);
(Continued)

(58) Field of Classification Search
CPC ...... G09B 23/303; G09B 23/30; G09B 23/34; G09B 23/285; G09B 23/32; A61B 34/30; A61B 17/00234; A61B 17/0483; A61B 17/062; A61B 17/42; A61B 2017/00716; A61B 2017/4216
USPC ........................................................ 434/268
See application file for complete search history.

(56) References Cited

U.S. PATENT DOCUMENTS

| | | | |
|---|---|---|---|
| 8,764,452 B2 * | 7/2014 | Pravong | G09B 23/306 434/272 |
| 9,373,270 B2 | 6/2016 | Miyazaki | |

(Continued)

FOREIGN PATENT DOCUMENTS

CN      203038547 U  *  7/2013

OTHER PUBLICATIONS

McConnon, A. How 3-D Printing Is Changing Health Care. Retrieved from https://www.wsj.com/articles/how-3-d-printing-is-changing-health-care-1505268301. Sep. 12, 2017. 4 pp.
(Continued)

*Primary Examiner* — Robert P Bullington
(74) *Attorney, Agent, or Firm* — Myers Bigel, P.A.

(57) ABSTRACT

The present disclosure describes a surgical training model that emulates a human pelvis for robotic, laparoscopic, and/or abdominal/open approach surgical training. Methods of performing a simulated surgery using the surgical training model are also provided.

16 Claims, 25 Drawing Sheets

(51) Int. Cl.
  *G09B 23/32* (2006.01)
  *A61B 17/42* (2006.01)
  *A61B 17/062* (2006.01)
  *A61B 17/04* (2006.01)

(52) U.S. Cl.
  CPC .... *A61B 2017/4216* (2013.01); *G09B 23/285* (2013.01); *G09B 23/32* (2013.01)

(56) References Cited

U.S. PATENT DOCUMENTS

| | | | |
|---|---|---|---|
| 9,830,834 B2 | 11/2017 | Miyazaki | |
| 2005/0214727 A1* | 9/2005 | Stoianovici | G09B 23/28 434/262 |
| 2007/0043338 A1* | 2/2007 | Moll | A61B 17/062 606/1 |
| 2011/0091855 A1* | 4/2011 | Miyazaki | G09B 23/303 434/267 |
| 2011/0174313 A1* | 7/2011 | von Pechmann | A61F 2/0063 128/834 |
| 2012/0034587 A1* | 2/2012 | Toly | G09B 23/285 434/267 |
| 2012/0282583 A1* | 11/2012 | Thaler | G09B 23/30 434/267 |
| 2014/0011172 A1* | 1/2014 | Lowe | G09B 23/281 434/273 |
| 2014/0248596 A1* | 9/2014 | Hart | G09B 23/285 434/272 |
| 2016/0104394 A1* | 4/2016 | Miyazaki | G09B 23/34 434/272 |
| 2016/0365007 A1* | 12/2016 | Black | G09B 23/285 |
| 2017/0296811 A1* | 10/2017 | Sharma | A61N 1/05 |

OTHER PUBLICATIONS

Tunitsky-Bitton, E. et al., Development and Validation of a Laparoscopic Sacrocolpopexy Simulation Model for Surgical Training, The Journal of Minimally Invasive Gynecology, vol. 21, Issue 4, Jul.-Aug. 2014, pp. 612-618.

Tunitsky, E. et al., Development and Validation of a Ureteral Anastomosis Simulation Model for Surgical Training, Female Pelvic Medicine & Reconstructive Surgery, vol. 19, No. 6, Nov./Dec. 2013, pp. 346-351.

* cited by examiner

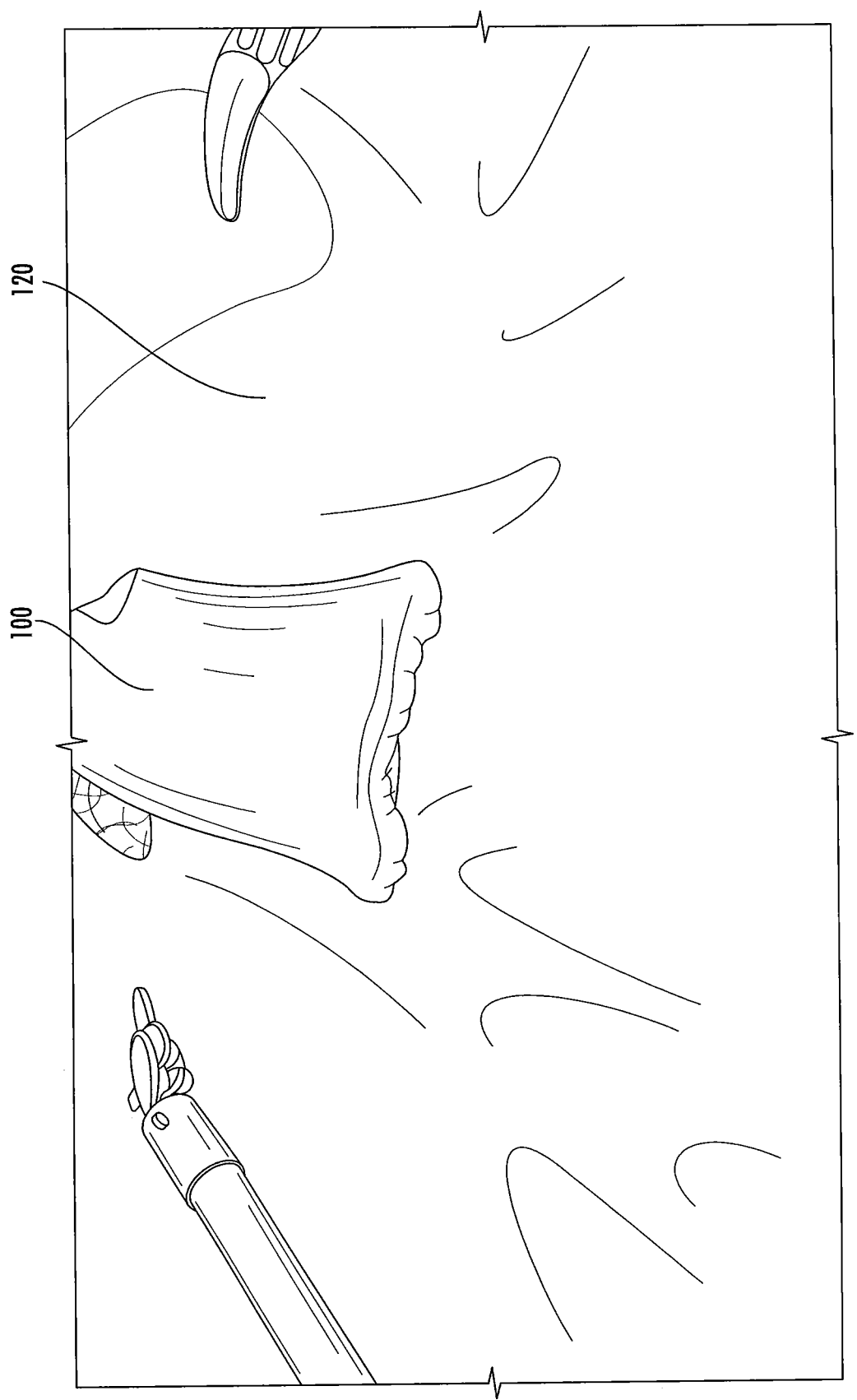

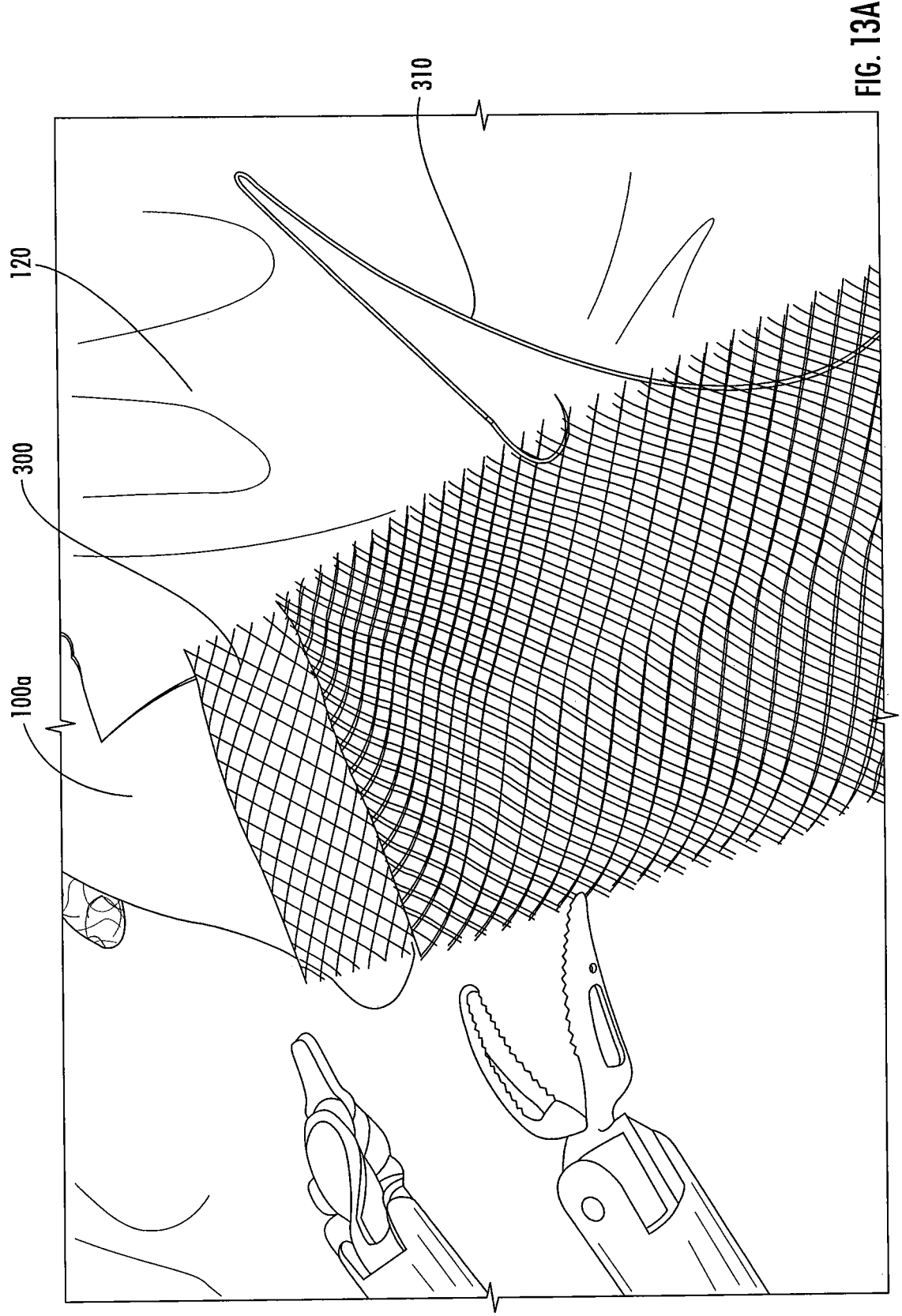

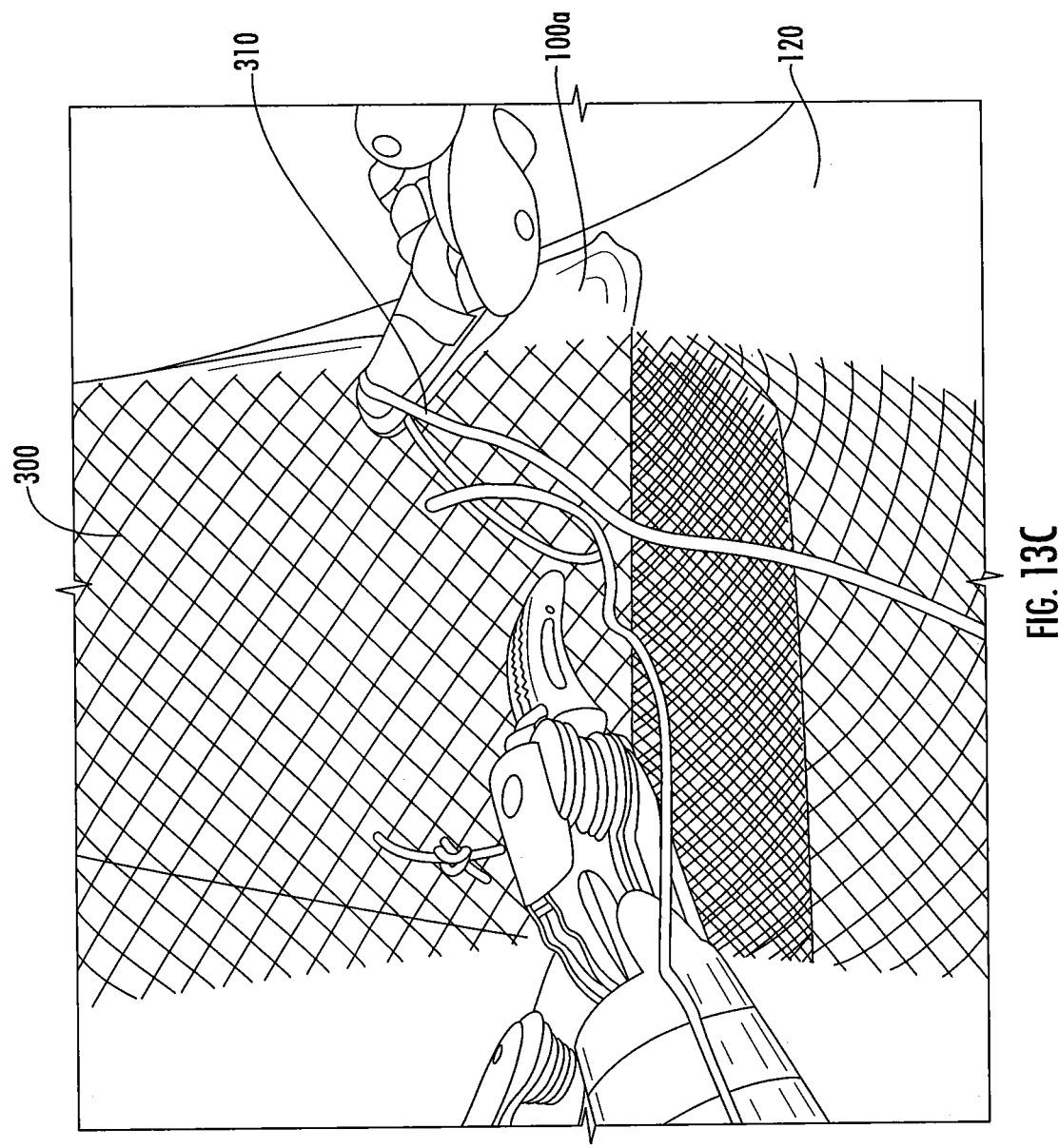

PELVIC MODEL FOR ROBOTIC, LAPAROSCOPIC, AND ABDOMINAL/OPEN APPROACH SURGICAL TRAINING

STATEMENT OF PRIORITY

This application claims the benefit, under 35 U.S.C. § 119(e), of U.S. Provisional Application Ser. No. 62/630,442, filed Feb. 14, 2018, the entire contents of which is incorporated by reference herein.

FIELD OF THE INVENTION

The invention relates to a surgical training model and methods for performing simulated procedures using the surgical training model. In particular, the invention relates to a pelvic model for robotic, laparoscopic, and abdominal/open approach surgical training for procedures such as, for example, sacrocolpopexy.

BACKGROUND OF THE INVENTION

Approximately 200,000 surgical procedures are performed annually for pelvic organ prolapse in the United States. Sacrocolpopexy is often offered to women who present with higher stages of prolapse. This mesh augmented procedure, while a more effective treatment for apical vaginal prolapse when compared to native tissue repair, is associated with a higher risk of mesh exposure and surgical injury. This procedure was traditionally performed via a laparotomy, but minimally invasive robotic and/or laparoscopic surgical approaches are now widely used to minimize pain for the patient, and improve recovery time. Proper training is necessary to develop the skills needed to safely perform this procedure with a minimally invasive approach.

To date, there are no standard dry lab training resources available for sacrocolpopexy which means training in this procedure is based on an apprenticeship model. It is necessary to dissect the presacral space during this procedure and identify the site of graft fixation at the level of S1 or S2 segment of the sacrum. Life-threatening hemorrhage can be encountered if any of the nearby vascular structures are compromised. Thus, there is a need for a simulation model to assist with training of novice surgeons in the procedure of robotic, laparoscopic, and abdominal/open approach sacrocolpopexy, as well as other pelvic surgeries, in a simulated training environment prior to performing the live surgery.

SUMMARY OF THE INVENTION

Embodiments of the present invention are directed to a surgical training model. In particular, some embodiments of the present invention are directed to a surgical training model comprising a pelvis model that emulates a human pelvis.

Some embodiments of the present invention are directed to a surgical training model for use in performing simulated surgeries using robotic, laparoscopic, and/or abdominal/open approach techniques.

Some embodiments of the present invention are directed to a surgical training model for use in performing simulated sacrocolpopexy surgery using robotic, laparoscopic, or abdominal/open approach techniques. The surgical training model may comprise a pelvis model that emulates a human pelvis, the pelvis model comprising a skeletal pelvis, an anterior longitudinal ligament, a middle sacral artery, an aorta, a common iliac artery, an internal iliac artery, an external iliac artery, a vena cava, a common iliac vein, a ureter, connective tissue, a peritoneum, and a vagina.

Some embodiments of the present invention are directed to a method of performing a simulated sacrocolpopexy surgery using robotic, laparoscopic, or abdominal/open approach techniques. The method may comprise providing a surgical training model, the surgical training model comprising a pelvis model that emulates a human pelvis, the pelvis model comprising a simulated skeletal pelvis, a simulated anterior longitudinal ligament, a simulated middle sacral artery, a simulated aorta, a simulated common iliac artery, a simulated internal iliac artery, a simulated external iliac artery, a simulated common iliac vein, a simulated ureter, simulated connective tissue, a simulated peritoneum, and a simulated vagina; positioning the surgical training model within an abdominal wall model, wherein the abdominal wall model optionally comprises apertures defined therein that are configured to receive a laparoscope and/or instrumentation associated with robotic and/or laparoscopic surgery; optionally receiving the laparoscope and/or instrumentation associated with robotic and/or laparoscopic surgery in the abdominal wall model through the apertures; dissecting the simulated peritoneum and simulated connective tissue; attaching a mesh to an anterior wall of the simulated vagina; attaching the mesh to a posterior wall of the simulated vagina; attaching the mesh to the simulated anterior longitudinal ligament; and suturing closed the simulated peritoneum over the mesh.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 9 is a top perspective view from a robotic camera of the surgical training model shown in FIG. 1 in use.

FIGS. 13A-E are top perspective views from a robotic camera of the surgical training model shown in FIG. 1 in use.

DETAILED DESCRIPTION OF THE INVENTION

Figure 1:
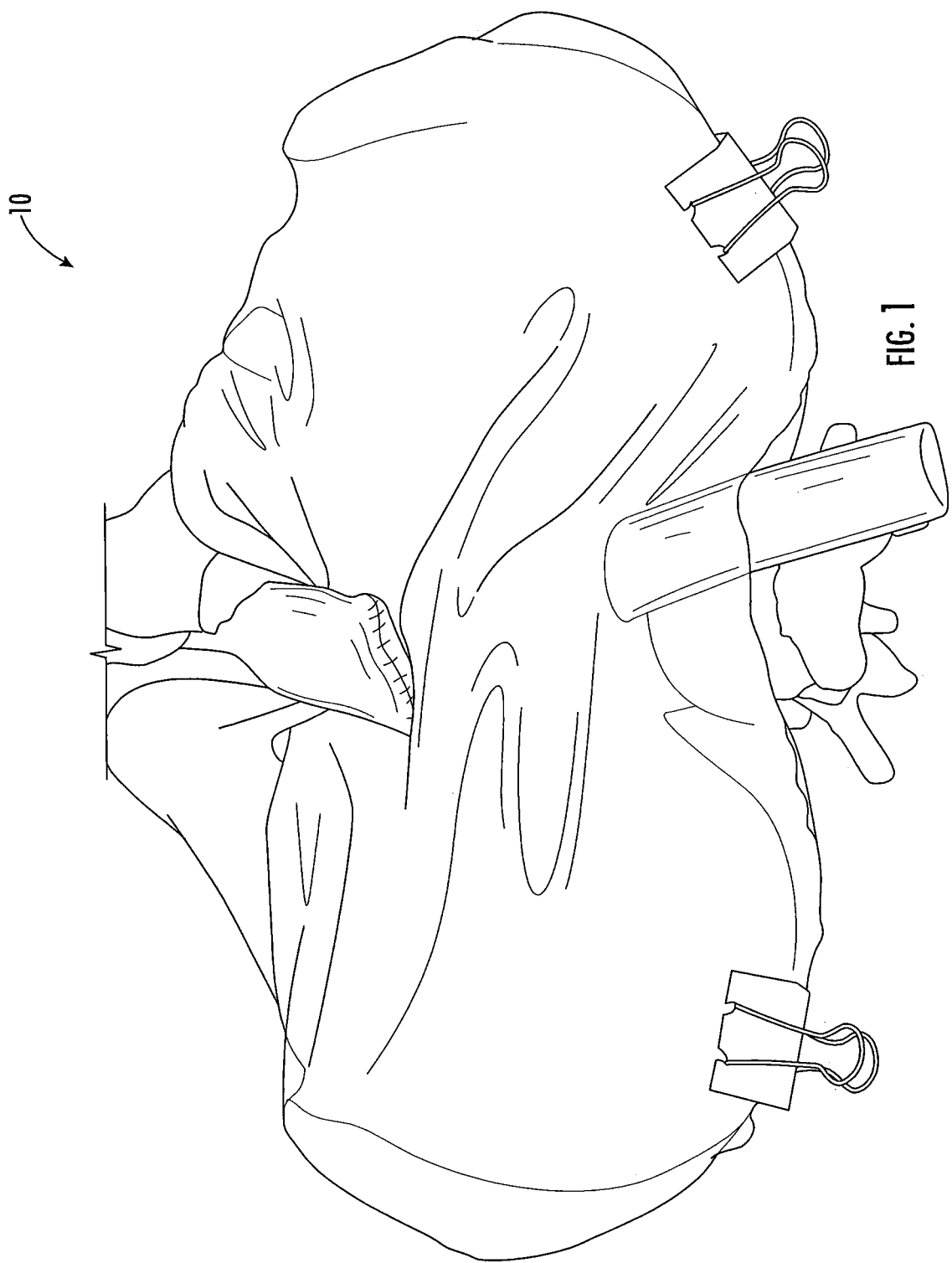
FIG. 1 is a top perspective view of a surgical training model according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Referring now to the figures, FIG. 1 shows a surgical training model 10 according to some embodiments of the present invention. The surgical training model 10 emulates a human pelvis and may be used to perform simulated surgical operations involving the pelvic anatomy. Types of simulated surgical operations include, but are not limited to, hysterectomy, oophorectomy, ovarian cystectomy, salpingectomy, sacrocolpopexy, uterosacral ligament suspension, ureteral reimplantation (ureteroneocystostomy, Psoas Hitch, Boari flap, ureteroureterostomy, transureteroureterostomy), vesicovaginal fistula repair, rectovaginal fistula repair, colon resection and reanastomosis, rectopexy, prostate surgery, Burch urethropexy, pelvic lymph node dissection, sacrospinous ligament release, hypogastric nerve ligation, endometriosis resection, hysterectomy with or without oophorectomy, and myomectomy and abdominal/open approaches to each of the above. The surgical training model 10 allows novice and experienced surgeons to practice robotic, laparoscopic, and/or abdominal/open approach skills in a simulation environment prior to performing a live surgery.

Figure 2:
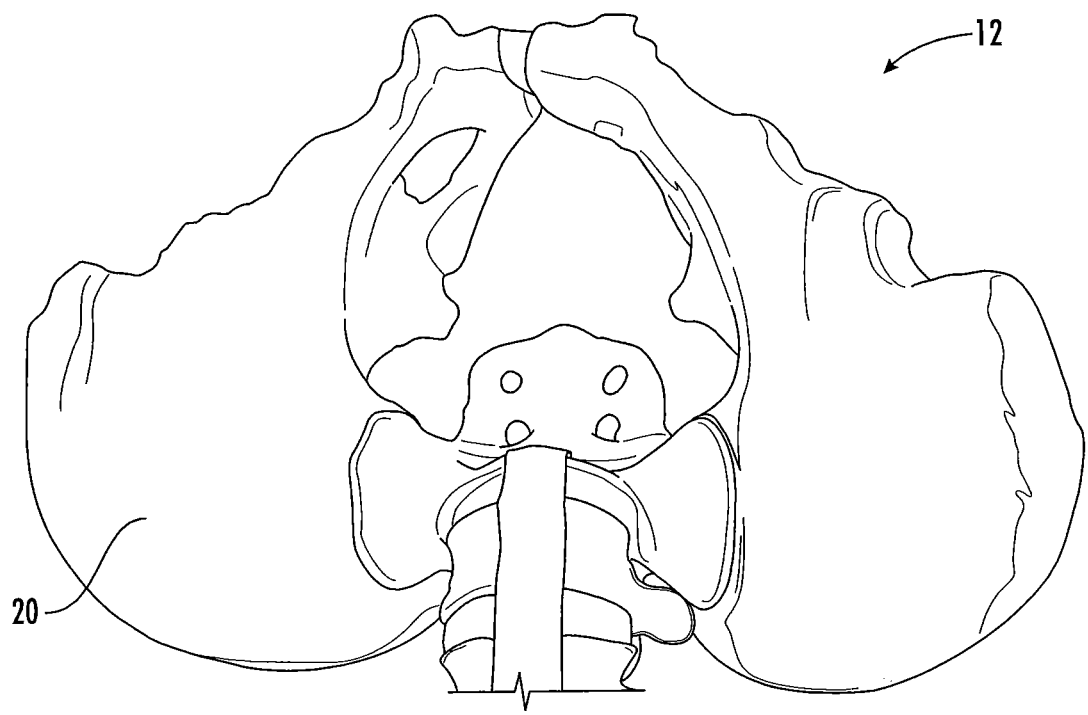
FIG. 2 is a top perspective view of a pelvis model of the surgical training model shown in FIG. 1.

FIGS. 1-7B illustrate the construction of the surgical training model 10 according to some embodiments of the present invention. Referring to FIG. 2, the surgical training model 10 includes a pelvis model 12. The pelvis model 12 emulates a human pelvis and includes a skeletal pelvis 20. The skeletal pelvis 20 may have the same basic anatomic parts of a human pelvis, such as ilium, ischial spine, public symphysis, ischium, coccyx, sacrum, sacral promontory, iliac crest, vertebra, and intervertebral disks. The skeletal pelvis 20 may include additional anatomic parts of a human pelvis that are not listed. The skeletal pelvis 20 may be formed from a variety of materials that can emulate the hardness of a human pelvis, such as bone, plastic and the like. In some embodiments, the skeletal pelvis 20 may be formed by 3D-printing methods. In some embodiments, the skeletal pelvis 20 may be reusable. "Reusable" as used herein means that the simulated anatomical part of the surgical training model 10 can be used for multiple simulated surgeries without having to create a new one.

Figure 3:
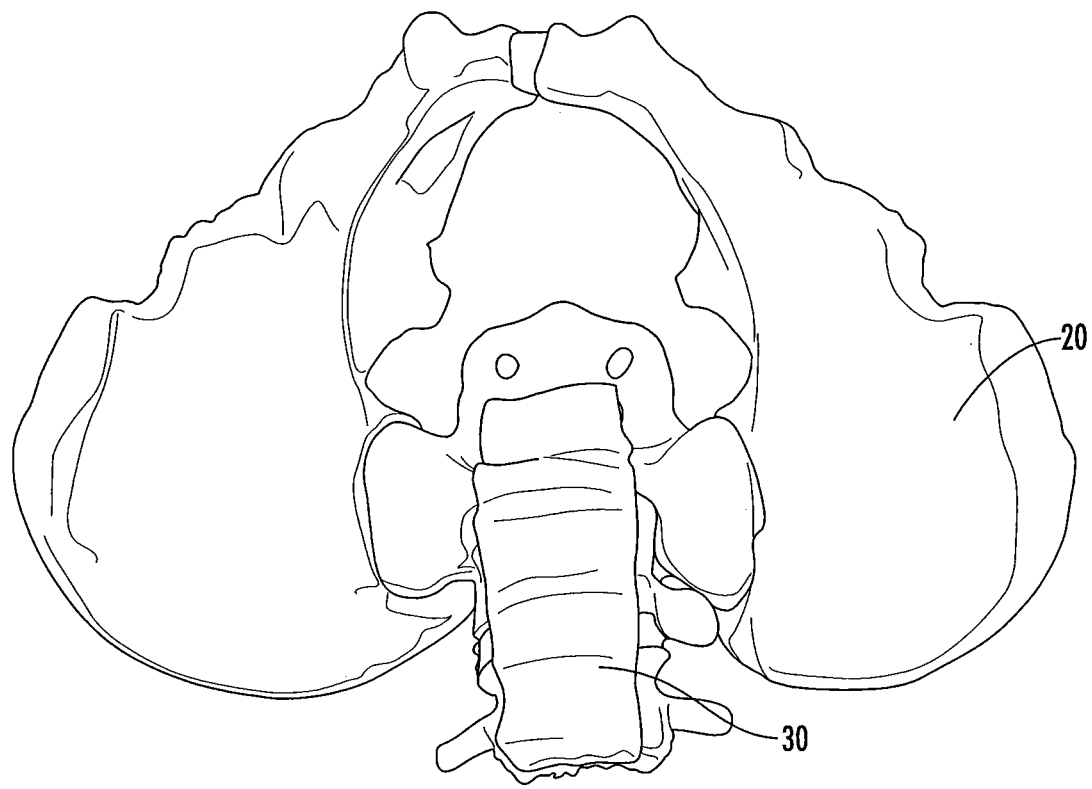
FIG. 3 is a top perspective view of the pelvis model shown in FIG. 2 with an anterior longitudinal ligament.

In some embodiments, the surgical training model 10 may include an anterior longitudinal ligament 30 (FIG. 3). In some embodiments, the anterior longitudinal ligament 30 may be releasably attached to the skeletal pelvis 20. "Releasably attached" as used herein means that the simulated anatomical part of the surgical training model 10 can be removed from and reinserted into or attached to the surgical training model 10 without causing damage to the part. The anterior longitudinal ligament 30 may be formed from a variety of materials that can emulate the viscoelasticity of human ligaments, such as medical tape, formulated plastics or the like. In FIG. 3, a piece of medical tape is used to represent the anterior longitudinal ligament 30. In some embodiments, the anterior longitudinal ligament 30 may be formed by 3D-printing methods. In some embodiments, the anterior longitudinal ligament 30 may be reusable.

Figure 4A:
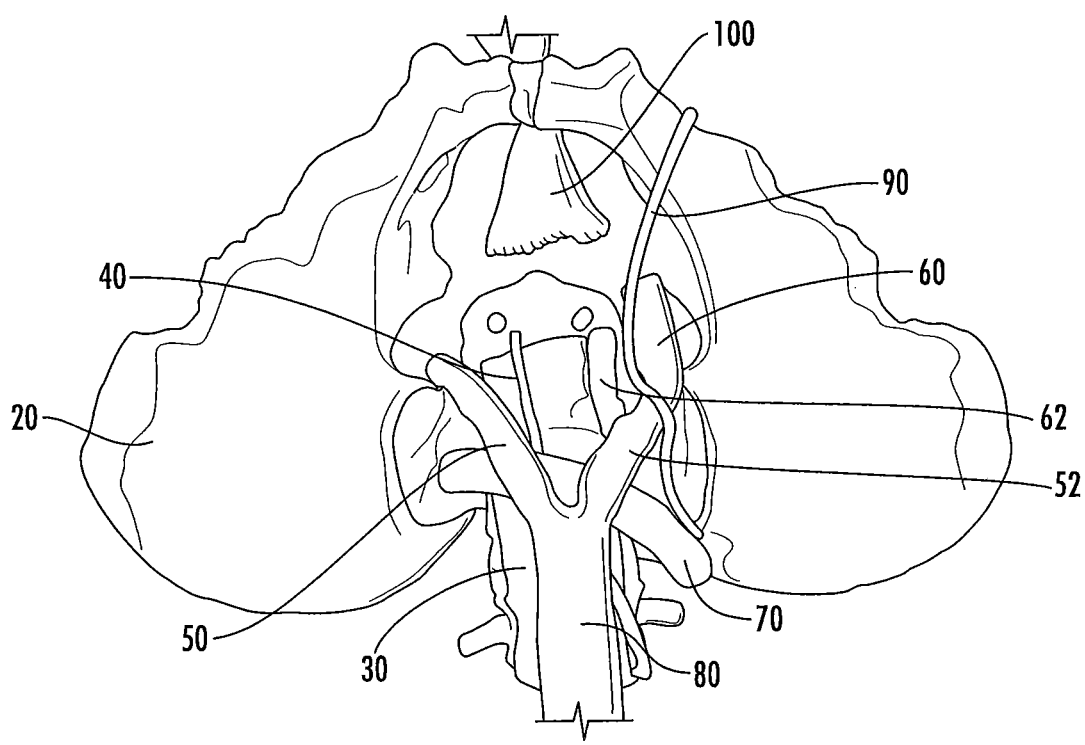
FIG. 4A is a top perspective view of the pelvis model shown in FIG. 2 with a middle sacral artery, right and left common iliac arteries, internal and external iliac arteries, a left common iliac vein, an aorta, a ureter, and a vagina cuff (post hysterectomy).
Figure 4B:
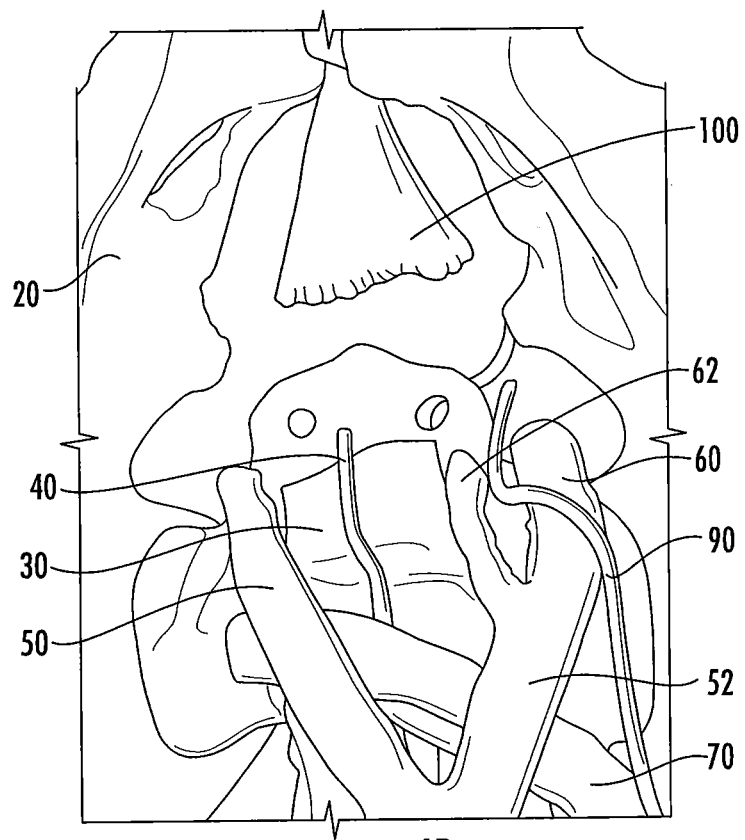
FIG. 4B is an enlarged top perspective view of the pelvis model shown in FIG. 4A.

As shown in FIGS. 4A and 4B, in some embodiments, the surgical training model 10 may include a middle sacral artery 40, right and left common iliac arteries 50, 52, internal and external iliac arteries 60, 62, a left common iliac vein 70, an aorta 80, a ureter 90, and a vagina cuff 100. Note that the vagina cuff 100 simulates the result of a prior hysterectomy. In some embodiments, the middle sacral artery 40, the right and left common iliac arteries 50, 52, the internal and external iliac arteries 60, 62, the left common iliac vein 70, the aorta 80, the ureter 90, and/or the vagina cuff 100 may be releasably attached to the pelvis model 12. These simulated anatomical parts of the surgical training model 10 may be releasably attached to the pelvis model 12 through the use of an adhesive (such as double-sided tape), VELCRO®, snaps or similar methods of attachment. The vasculature (e.g., the middle sacral artery 40, the right and left common iliac arteries 50, 52, the internal and external iliac arteries 60, 62, and the aorta) (or the obturator artery, nerve, and vein when considering Burch urethropexy), the ureter 90, and the vagina cuff 100 may be formed from a variety of materials that can emulate the texture and rigidity of these anatomical parts. Exemplary suitable materials that may be used include polymers or elastomers such as silicone rubber or the like. An example of silicone rubber that may be used is Ecoflex® (Smooth-On, Inc., Macungie, Pa.). These simulated anatomical parts may be solid or hollow depending on the needs of the surgical training lab. For example, a hollow vessel can be filled with a fluid to simulate possible surgical complications such as hemorrhage. In some embodiments, the vasculature (40, 50, 52, 60, 62, 70 and 80), the ureter 90 and the vagina cuff 100 may be formed by 3D-printing methods. In some embodiments, the middle sacral artery 40, the right and left common iliac arteries 50, 52, the internal and external iliac arteries 60, 62, the left common iliac vein 70, the aorta 80, the ureter 90, and/or the vagina cuff 100 may be reusable.

Figure 5A:
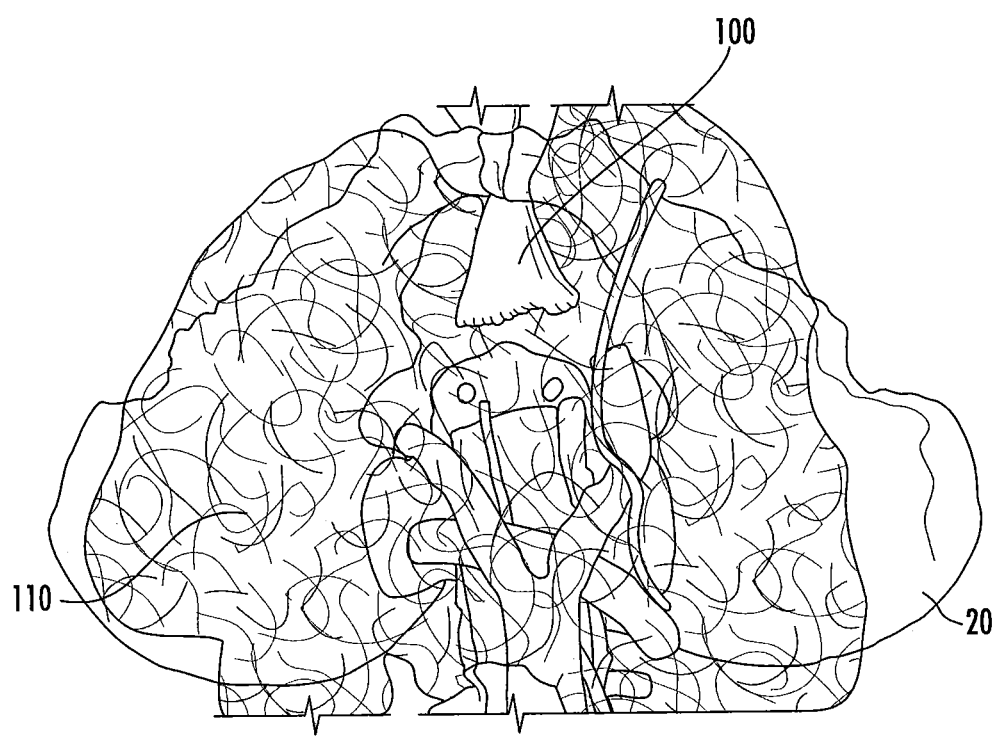
FIG. 5A is a top perspective view of the pelvis model shown in FIG. 4A with loose connective tissue/areolar tissue.
Figure 5B:
FIG. 5B is an enlarged top perspective view of the pelvis model shown in FIG. 5A.

Referring now to FIGS. 5A and 5B, in some embodiments, the surgical training model 10 may include loose connective tissue 110 (as known as areolar tissue). The loose connective tissue 110 covers the vasculature (40, 50, 52, 60, 62, 70 and 80) and the ureter 90 (as seen in FIGS. 4A and 4B), but goes underneath the vagina cuff 100 (FIG. 5B). In some embodiments, the bladder can be in place anterior to the vaginal cuff 100 and descending colon behind the vaginal cuff 100 with loose connective tissue 110 between each structure. In some embodiments, the loose connective tissue 110 may be adhered to the pelvis model 12. In other embodiments, the loose connective tissue 110 may be releasably attached to the pelvis model 12. The loose connective tissue 110 may be formed from a variety of non-woven materials that can emulate the texture of areolar tissue, such as cotton, polyester, wool, acrylic, plastics, or the like. In FIGS. 5A and 5B, a non-woven cotton or polyester quilt batting is used to represent the loose connective tissue 110.

Figure 6:
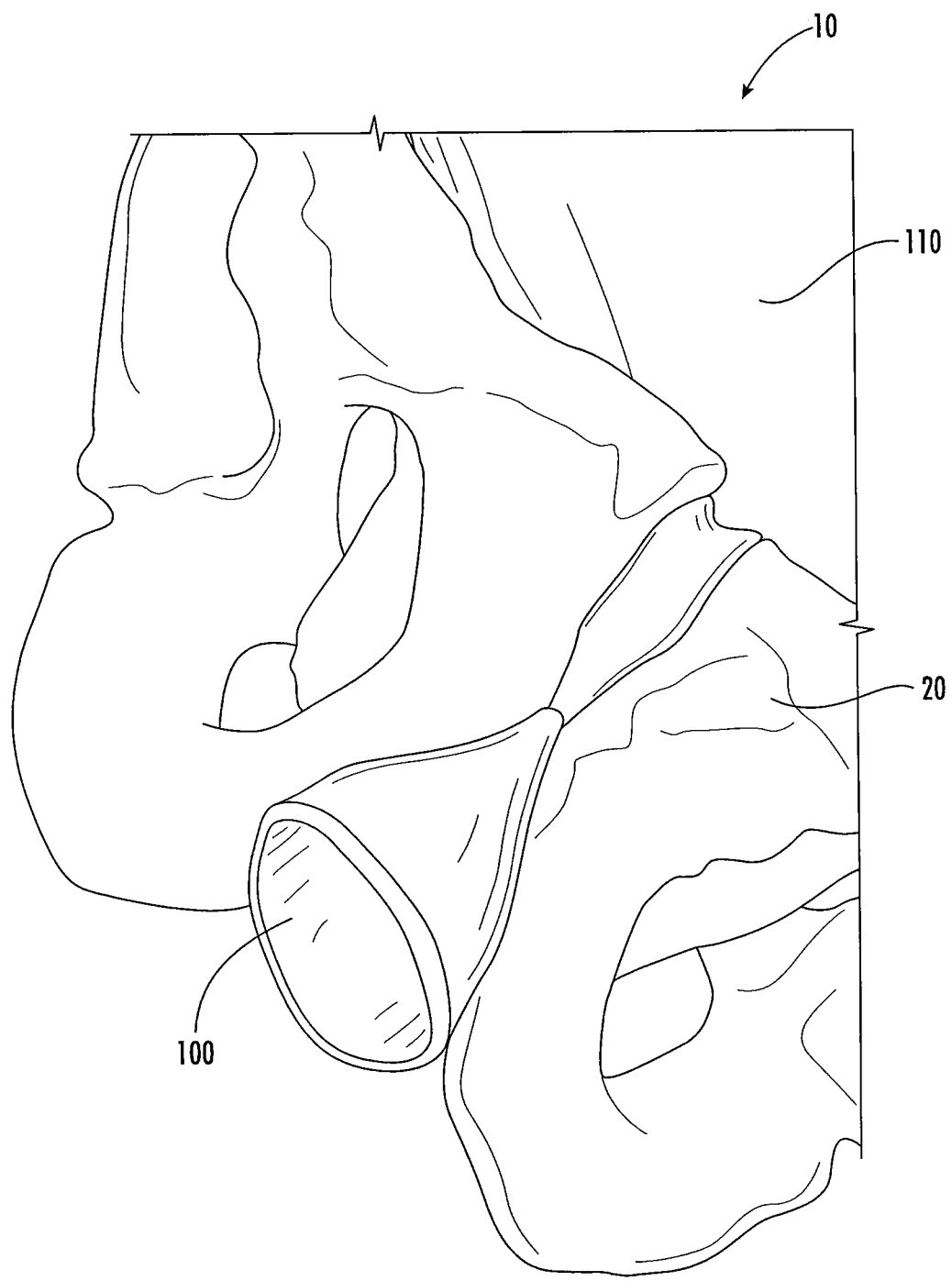
FIG. 6 is a bottom perspective view of the pelvis model shown in FIG. 5A.

FIG. 6 shows a bottom perspective of the surgical training model 10. As seen in FIG. 6, the external portion of the vaginal cuff 100 is secured to the skeletal pelvis 20. The vaginal cuff 100 may be secured to the skeletal pelvis 20 by wedging the cuff 100 below the pubic symphysis of the skeletal pelvis 20.

Figure 7A:
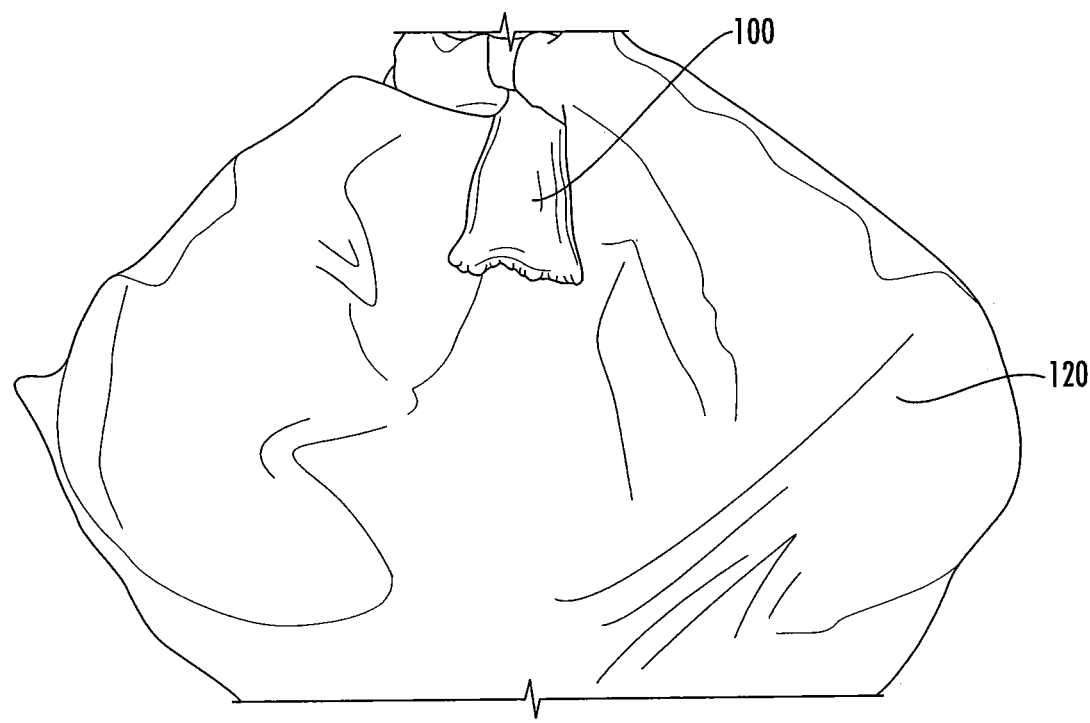
FIG. 7A is a top perspective view of the pelvis model shown in FIG. 5A with a peritoneum.
Figure 7B:
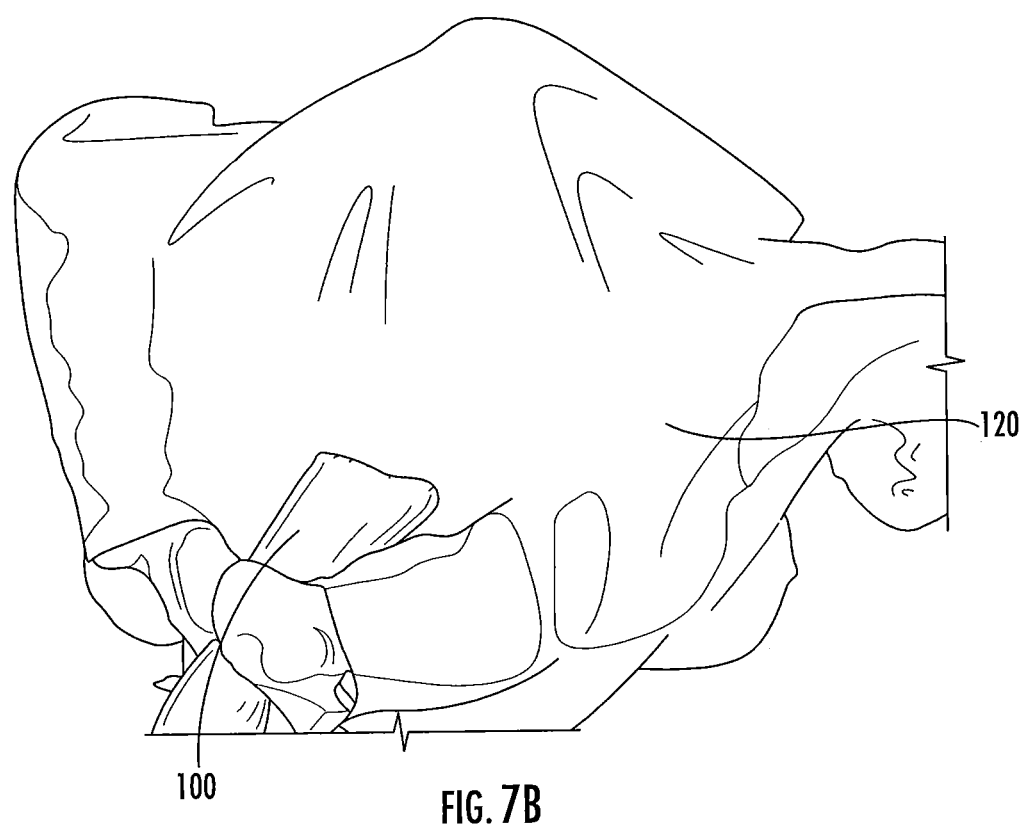
FIG. 7B is an alternate top perspective view of the pelvis model shown in FIG. 7A.

As shown in FIGS. 7A and 7B, in some embodiments, the surgical training model 10 may include a peritoneum layer 120. The peritoneum 120 covers the loose connective tissue 110, and similar to the placement of the loose connective tissue 110, the peritoneum 120 goes underneath the vagina cuff 100 (FIG. 5B). The peritoneum 120 may be formed from a variety of materials that can emulate the texture of the membrane that forms the lining of the abdominal cavity. Exemplary suitable materials used may include polymers or elastomers such as silicone rubber or the like. An example of silicone rubber that may be used is Ecoflex® (Smooth-On, Inc., Macungie, Pa.). The peritoneum 120 may be adhered or otherwise attached to an outer periphery or outer peripheral portion of the pelvis model 12. In some embodiments, the peritoneum 120 may be formed by 3D-printing methods. In some embodiments, the peritoneum 120 may be releasably attached to the pelvis model 12.

For most simulated surgical procedures performed using the surgical training model 10 of the present invention, the peritoneum 120 is dissected (i.e., cut/opened) and therefore will have to be replaced prior to using the surgical training model 10 for another simulated surgical procedure. An exception would be when the surgical training model 10 is used to simulate a hysterectomy procedure. In a simulated hysterectomy procedure, it is not necessary to dissect the peritoneum 120. Therefore, in these situations, the peritoneum 120 may be reused for the next simulated surgical procedure performed using the surgical training model 10.

In some embodiments, the pelvis model 12 of the surgical training model 10 may include additional simulated anatomical parts. These additional simulated anatomical parts may include, but are not limited to, sacral nerve roots, uterosacral ligaments, a bladder, a rectum, a uterus, ovaries/ fallopian tubes, a Cooper's Ligament (pectineal ligament), an obturator neurovascular bundle and obturator canal, a median and medial umbilical ligament, a Psoas muscle, a Psoas minor tendon, a femoral nerve, a genitofemoral nerve, a uterine serosa, a myometrium, a myoma, and/or a myoma capsule. Some or all of these simulated anatomical parts may be releasably attached to the pelvis model 12. In some embodiments, the sacral nerve roots, the uterosacral ligaments, the bladder, the rectum, the uterus, the ovaries/fallopian tubes, the Cooper's Ligament, the obturator neurovascular bundle and obturator canal, the median and medial umbilical ligament, the Psoas muscle, the Psoas minor tendon, the femoral nerve, the genitofemoral nerve, the uterine serosa, the myometrium, the myoma, and/or the myoma capsule may be reusable.

In some embodiments, the surgical training model 10 may be used with a robotic or laparoscopic surgical system 200. In other embodiments, the surgical training model 10 may be used to simulate an abdominal/open approach surgical procedure.

Figure 8A:
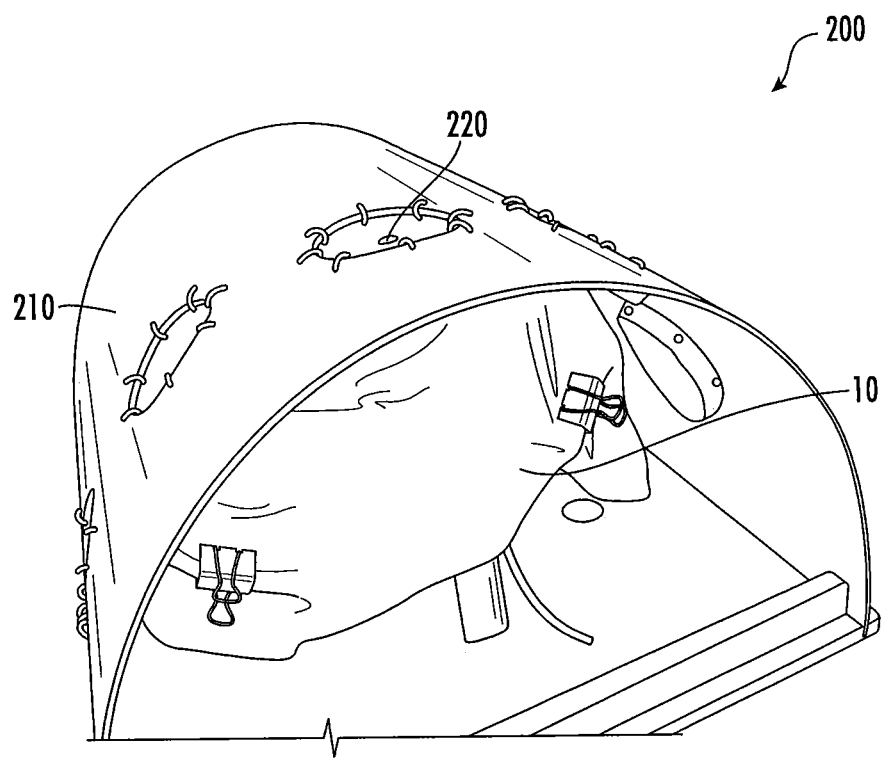
FIG. 8A is a top perspective view of the surgical training model shown in FIG. 1 shown inserted into an abdominal model for robotic surgical training.
Figure 8B:
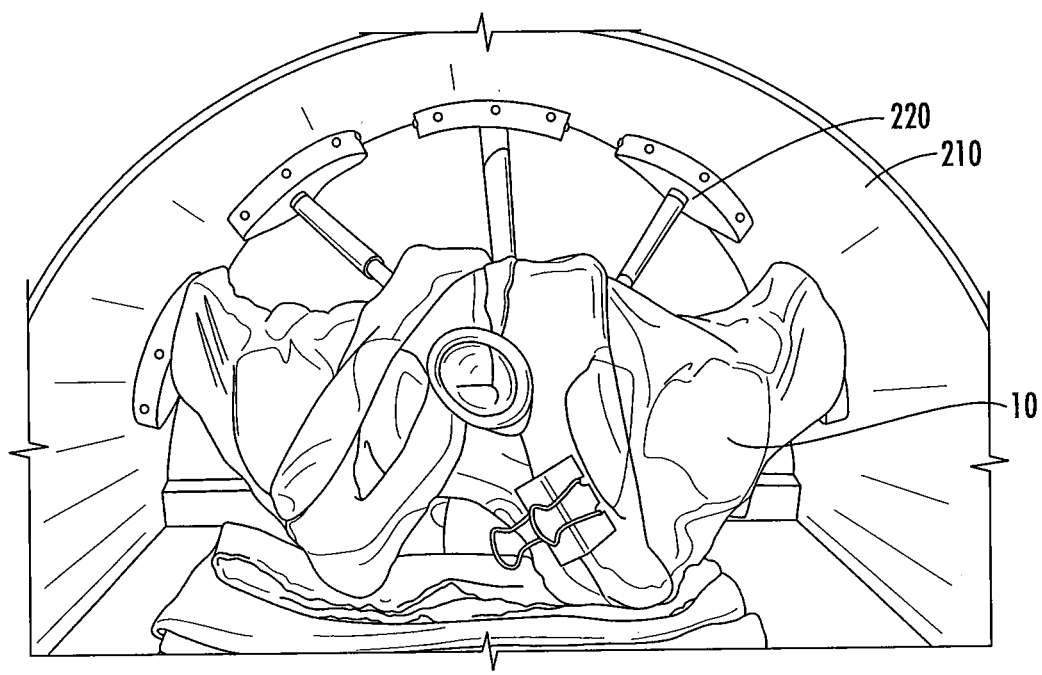
FIG. 8B is a bottom perspective view of the surgical training model shown in FIG. 8A.

As shown in FIGS. 8A and 8B, the surgical training model 10 may be used with an abdominal wall model 210. In some embodiments, the abdominal wall model 210 overlays the surgical training model 10. The abdominal wall model 210 may have apertures 220 defined therein that are configured to receive a robotic camera and/or instrumentation associated with robotic surgery. In other embodiments, the abdominal wall model 210 may be configured to receive a laparoscope and/or instrumentation associated with laparoscopic surgery. Further embodiments may utilize an abdominal model 210 that simulates an abdominal cavity to allow the surgical training model 10 to be used to simulate an abdominal/open approach to the surgical procedures disclosed above.

The surgical training model 10 in association with the abdominal wall model 210 allows both novice and experienced surgeons to practice robotic skills in a simulation environment. Further, laparoscopic and abdominal/open approach surgery skills can be practiced by both novice and experienced surgeons using a laparoscopic abdominal wall model and abdominal cavity model, respectively, in association with the surgical training model 10.

In some embodiments, the surgical training model 10 allows a surgeon to perform simulated sacrocolpopexy surgery using robotic, laparoscopic, and/or abdominal/open approach techniques. Sacrocolpopexy is a surgical technique for repairing pelvic organ prolapse. Pelvic organ prolapse is the symptomatic descent of one or more of components of the vaginal wall, including the anterior wall, posterior wall, and the vaginal apex, which could lead to descent of the cervix and uterus or the vaginal cuff following a hysterectomy. FIGS. 9 through 17 are based on digital images taken while a surgeon is performing a simulated sacrocolpopexy using the surgical training model 10 according to embodiments of the present invention.

Figure 10:
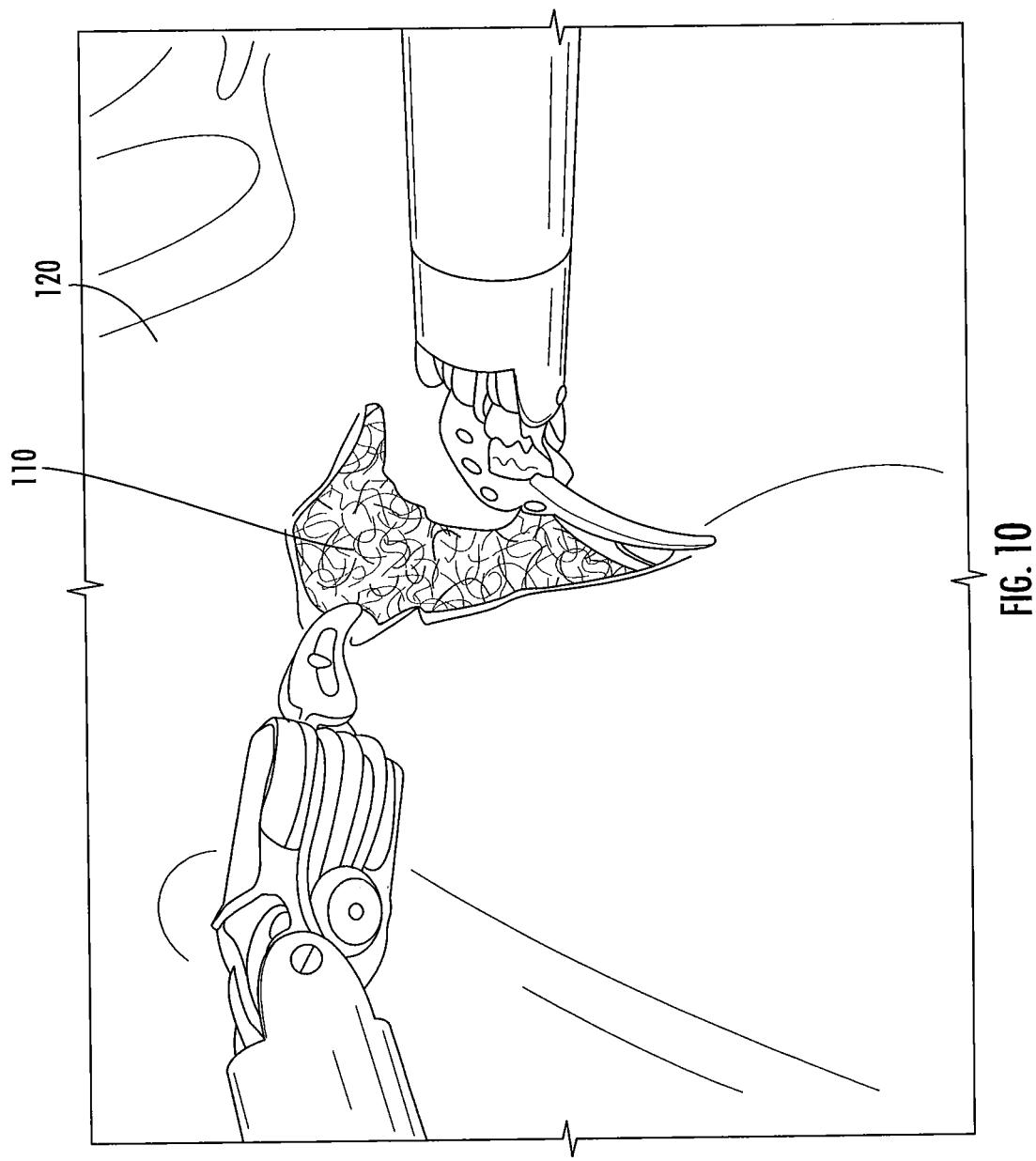
FIG. 10 is a top perspective view from a robotic camera of the surgical training model shown in FIG. 1 in use.
Figure 11:
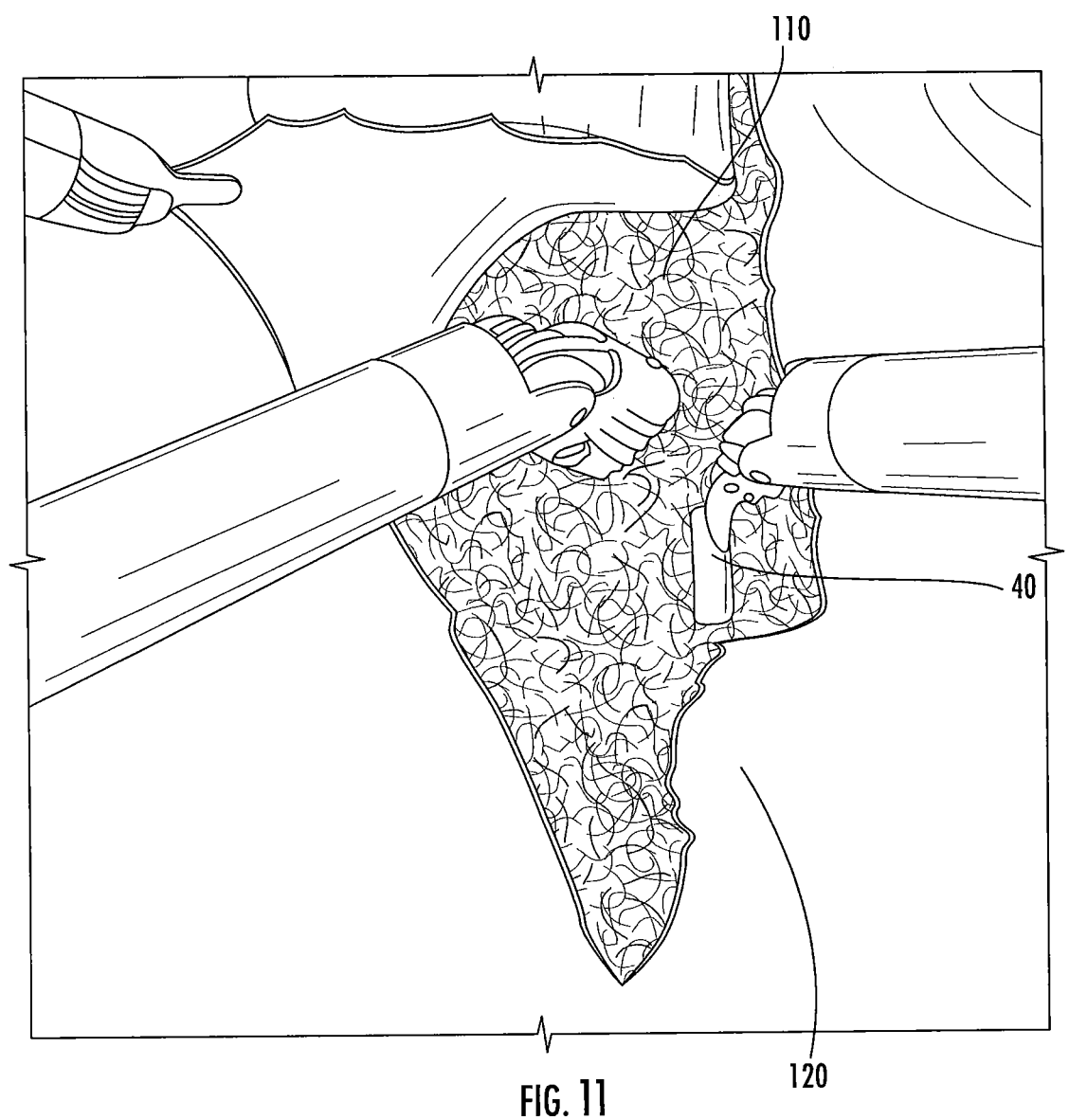
FIG. 11 is a top perspective view from a robotic camera of the surgical training model shown in FIG. 1 in use.

First referring to FIG. 9, a top perspective view from a robotic camera of the surgical training model 10 is shown. The surgeon begins the simulated sacrocolpopexy by tenting up the simulated peritoneum 120 at the sacrum and beginning the presacral dissection of the simulated peritoneum 120 (FIG. 10). In FIG. 10 and FIG. 11, the simulated loose connective tissue 110 can be seen underneath the simulated peritoneum 120 as the surgeon dissects the simulated peritoneum 120. The surgeon continues to dissect the simulated peritoneum 120 and simulated loose connective tissue 110 of the sacral promontory, being very careful to not puncture the simulated middle sacral artery 40.

Figure 12:
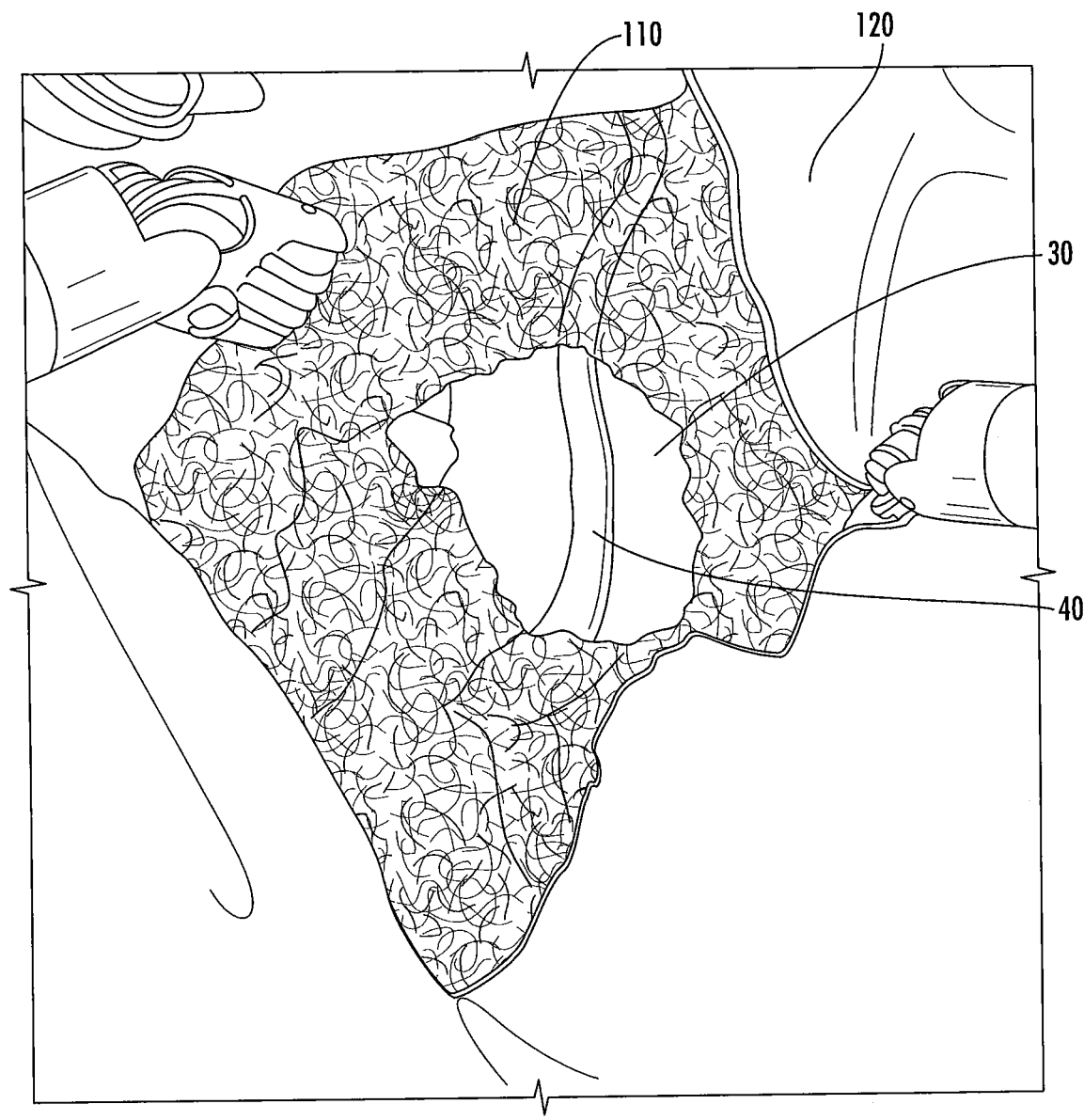
FIG. 12 is a top perspective view from a robotic camera of the surgical training model shown in FIG. 1 in use.

FIG. 12 shows the completed presacral dissection of the simulated peritoneum 120 and simulated loose connective tissue 110. Once completed, the surgeon should have a clear view of the simulated middle sacral artery 40 and simulated anterior longitudinal ligament 30.

The next step in the simulated sacrocolpopexy is to dissect the simulated peritoneum 120 from the sacral promontory to the simulated vagina cuff 100. In some embodiments, the surgical training model 10 may allow the simulation of dissecting away a simulated bladder superior and a simulated rectum posterior from the simulated vagina cuff 100 (not shown in the figures).

Figure 13B:
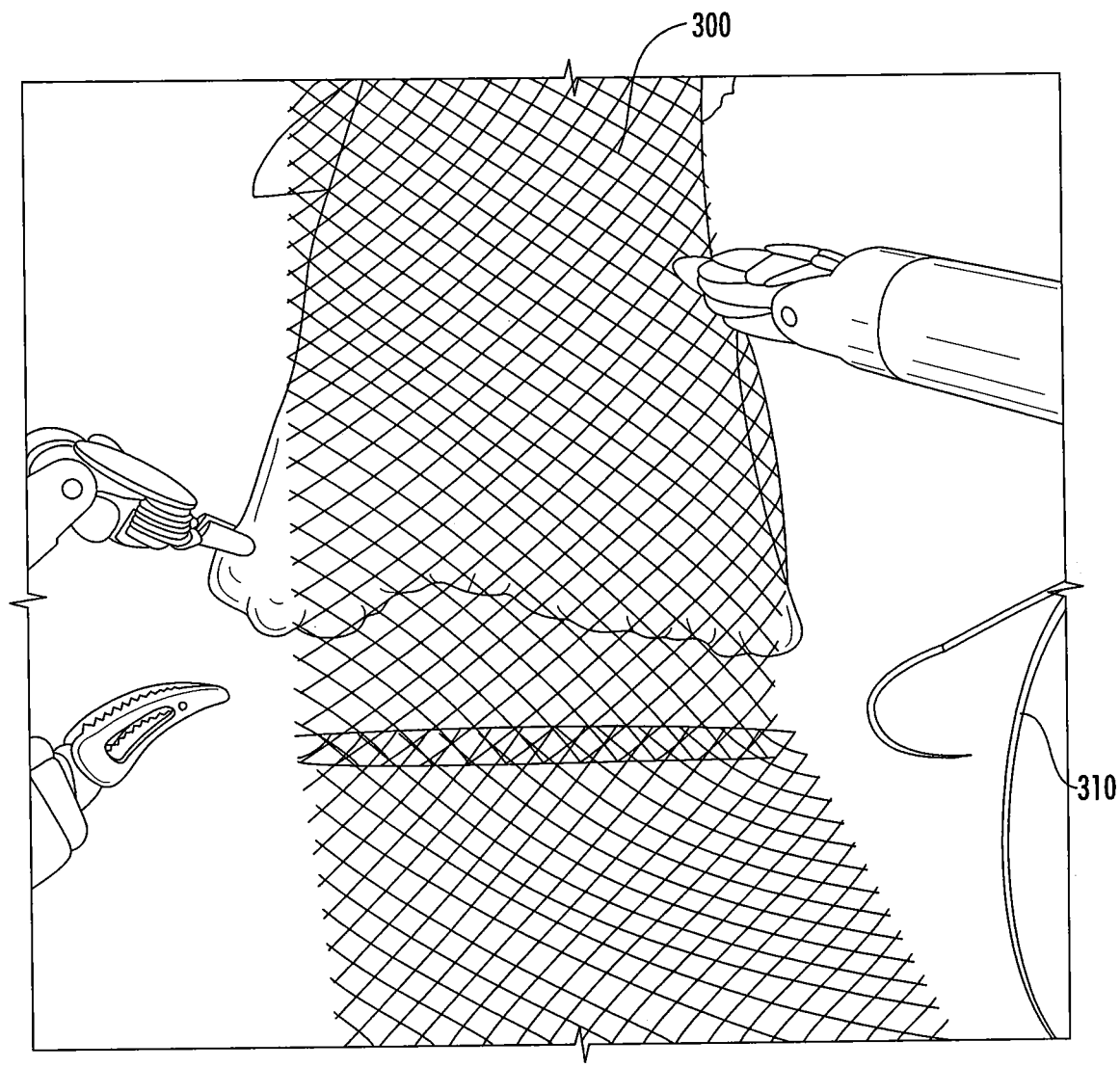
Figure 13D:
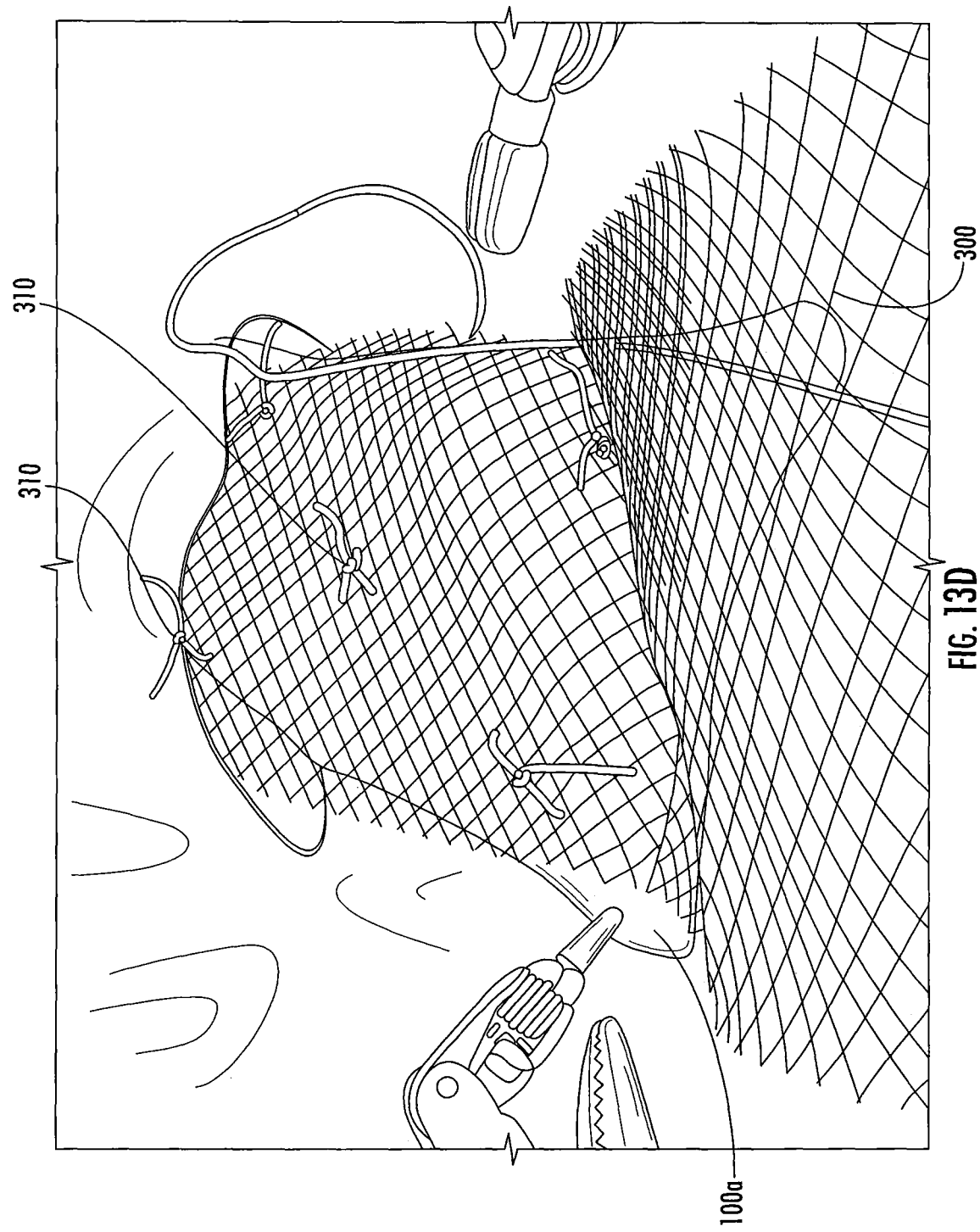

The next step in the simulated sacrocolpopexy surgery is attachment of a Y-shaped mesh from the simulated vagina cuff 100 to the sacral promontory. This step is illustrated in FIGS. 13-16. First, one of the arms of the Y-shaped mesh 300 is attached via sutures 310 to the anterior vaginal wall 100*a* (FIGS. 13B-13D). In some embodiments, the simulated sacrocolpopexy surgery allows the simulation of dissecting a simulated bladder (not shown in the figures) and a simulated rectum (not shown in the figures) away from the simulated vagina cuff 100 prior to attaching the mesh to the anterior vaginal wall 100*a*.

Figure 13E:
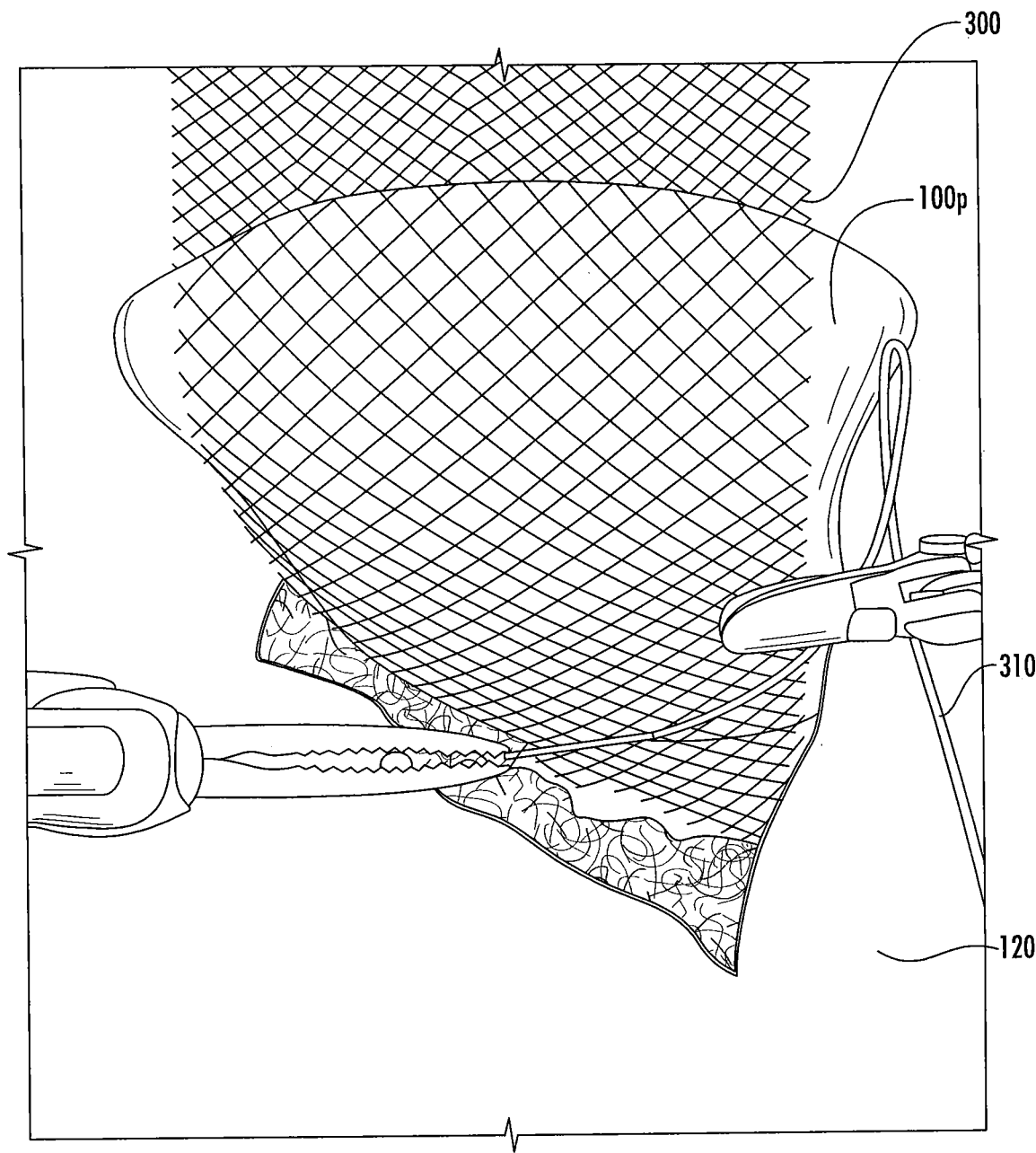
Figure 14:
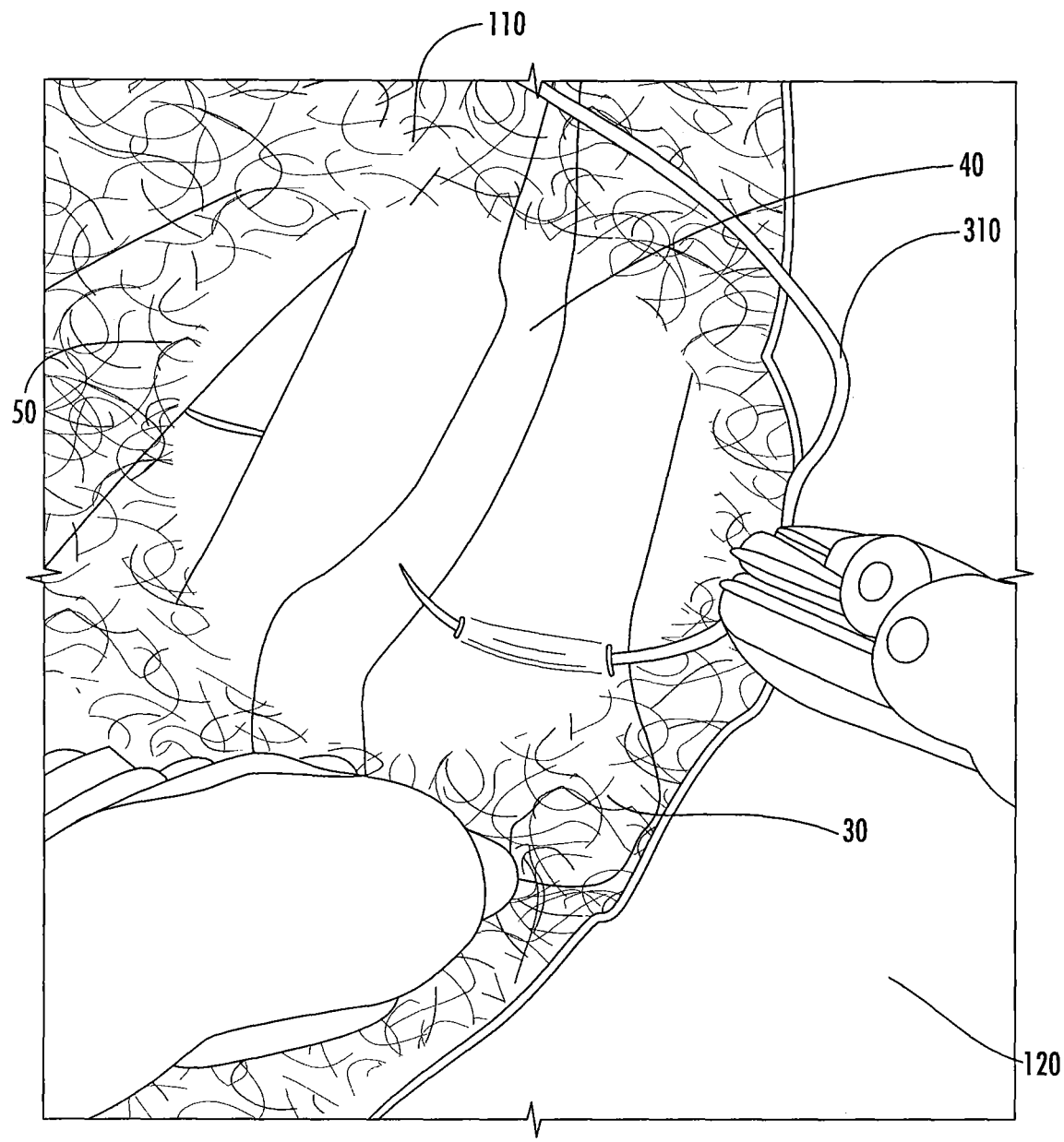
FIG. 14 is a top perspective view from a robotic camera of the surgical training model shown in FIG. 1 in use.
Figure 15A:
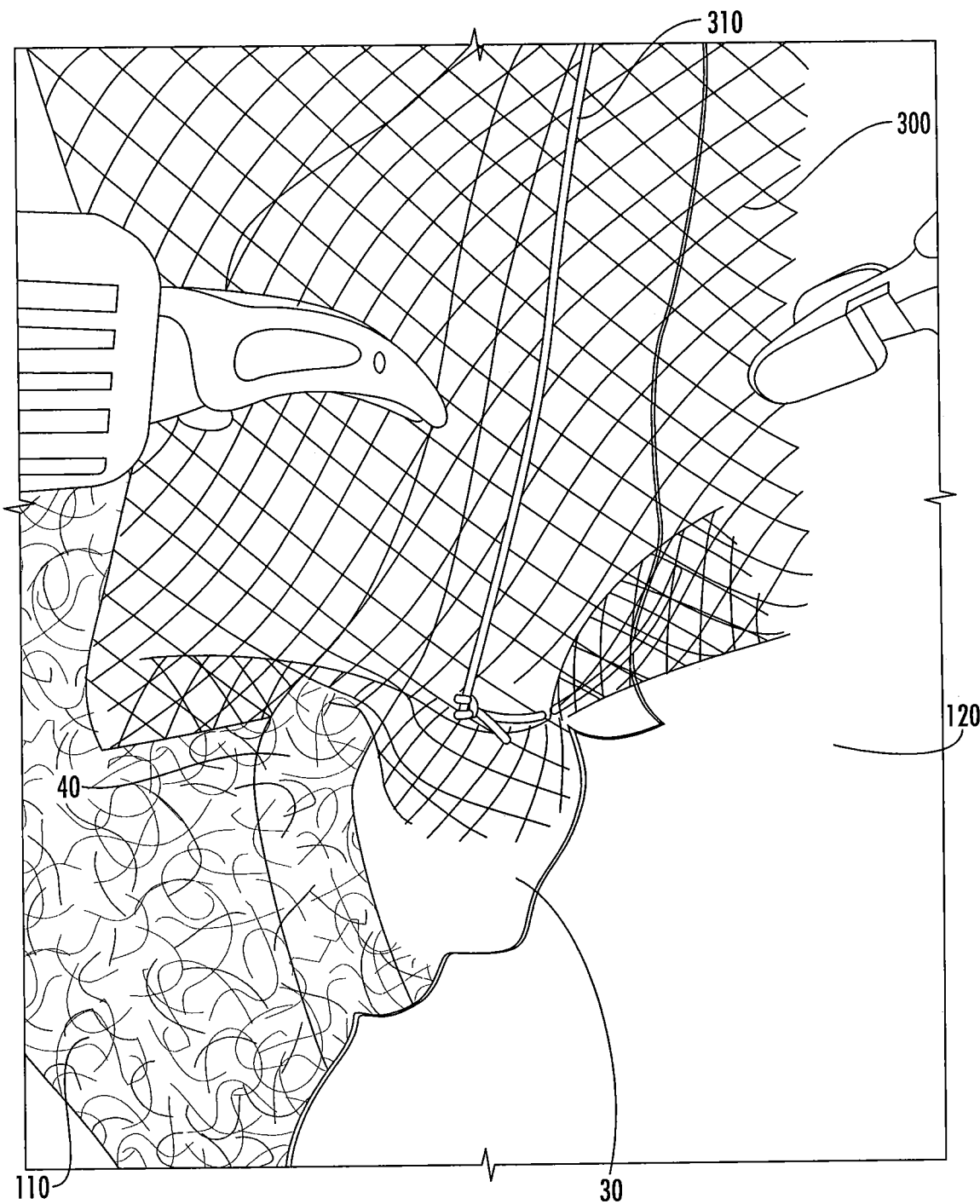
FIGS. 15A and 15B are top perspective views from a robotic camera of the surgical training model shown in FIG. 1 in use.
Figure 15B:
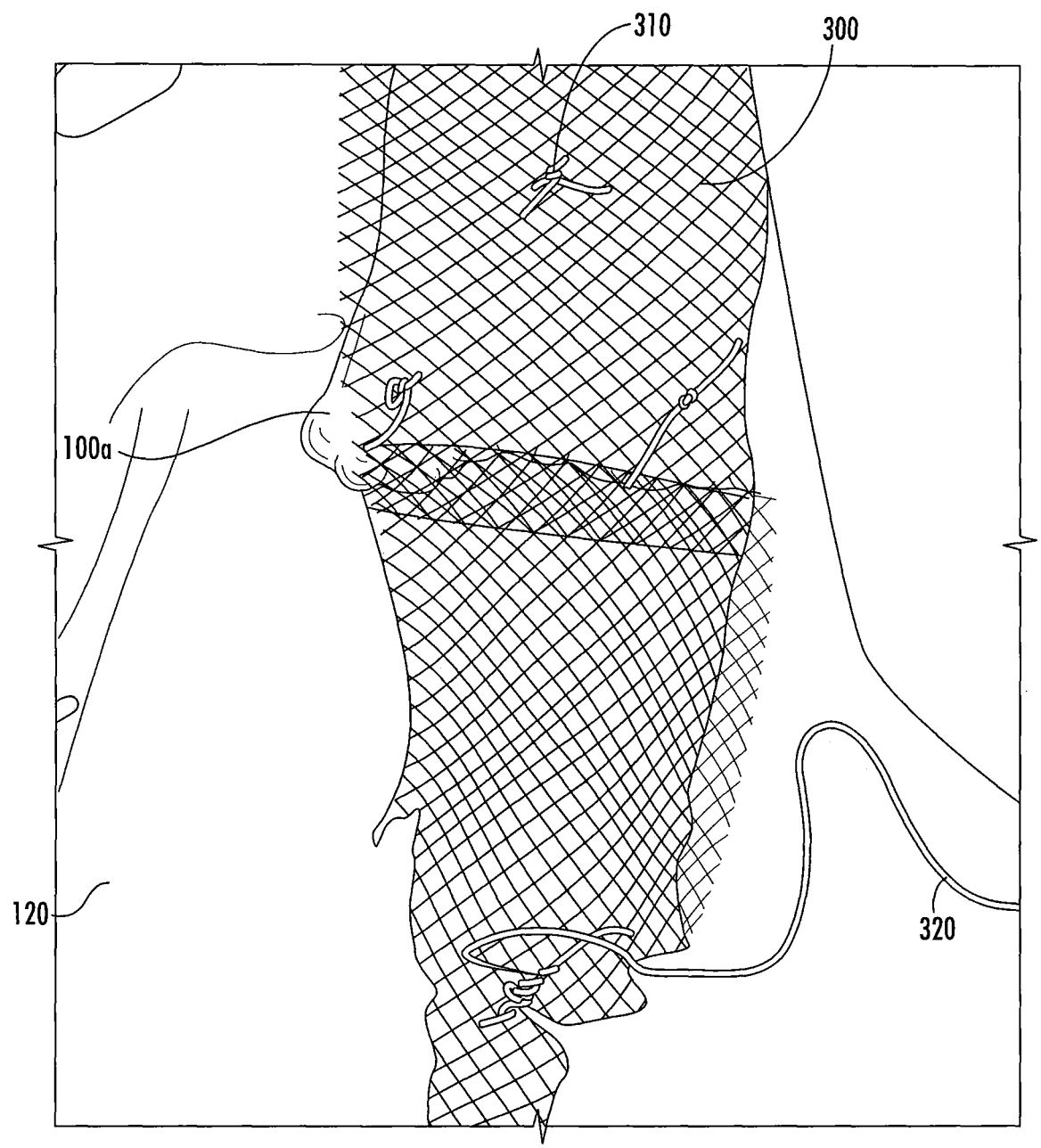

Next, the other arm of the Y-shaped mesh 300 is attached via sutures 310 to the posterior vaginal wall 100*p* (FIG. 13E). The bottom part of the Y-shaped mesh 300 is then attached via sutures 310 to the simulated anterior longitudinal ligament 30 (FIG. 14 and FIGS. 15A-15B). Again, the surgeon being very careful not to puncture the simulated middle sacral artery 40. FIG. 15B shows the completed simulated sacrocolpopexy with the Y-shaped mesh attached to the simulated vagina cuff 100 and the simulated anterior longitudinal ligament 30.

Figure 16A:
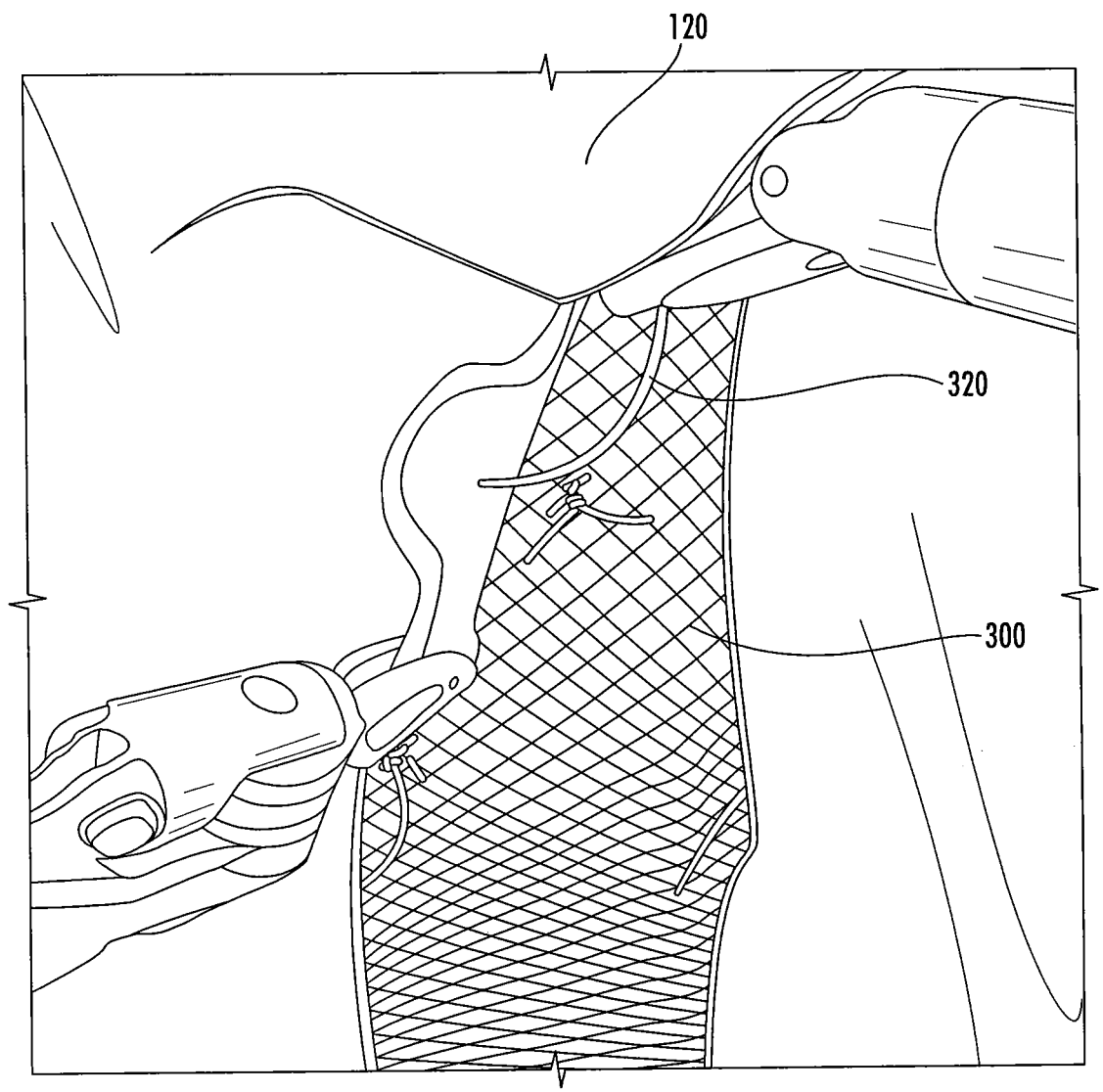
FIGS. 16A and 16B are top perspective views from a robotic camera of the surgical training model shown in FIG. 1 in use.
Figure 16B:
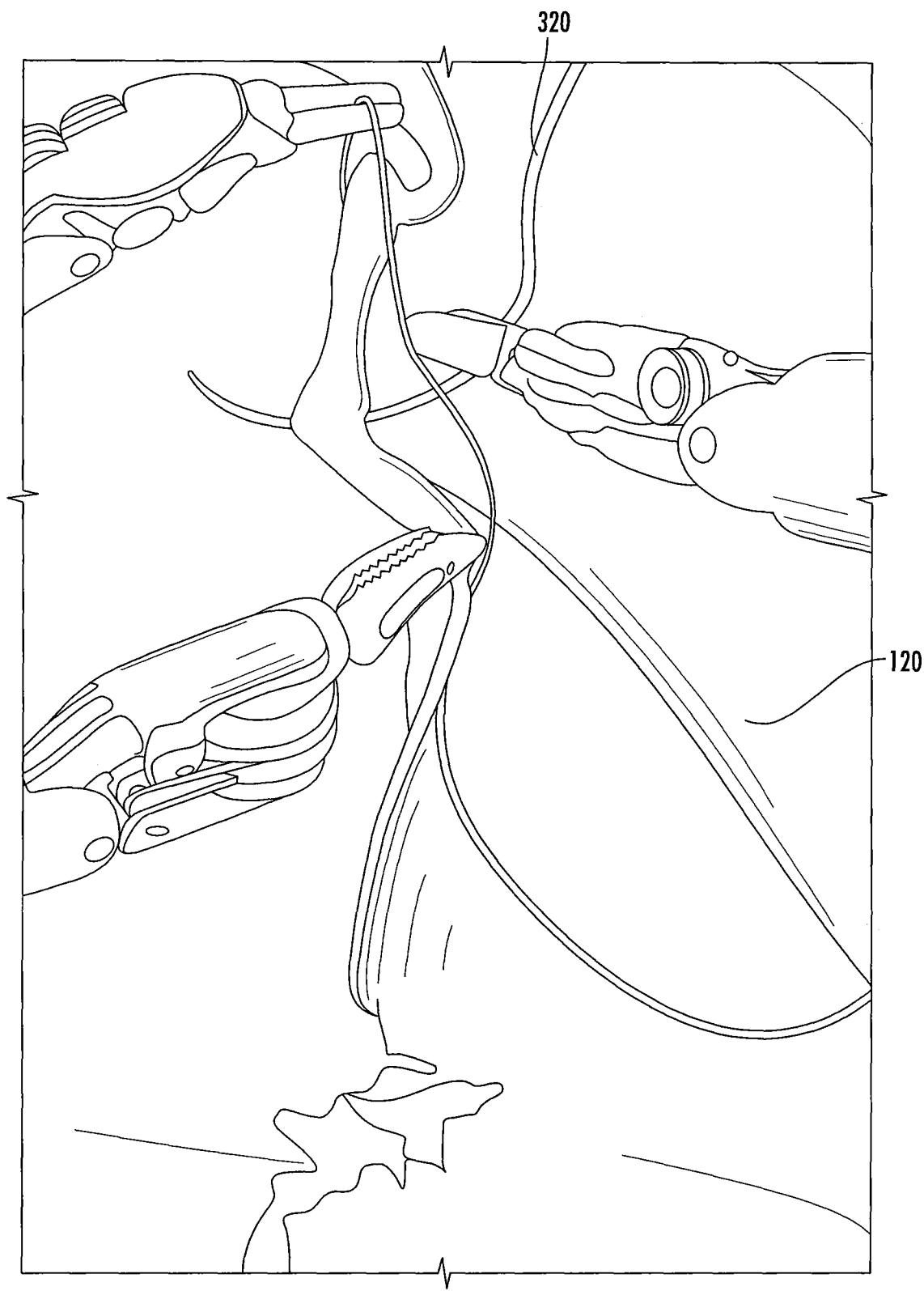
Figure 17:
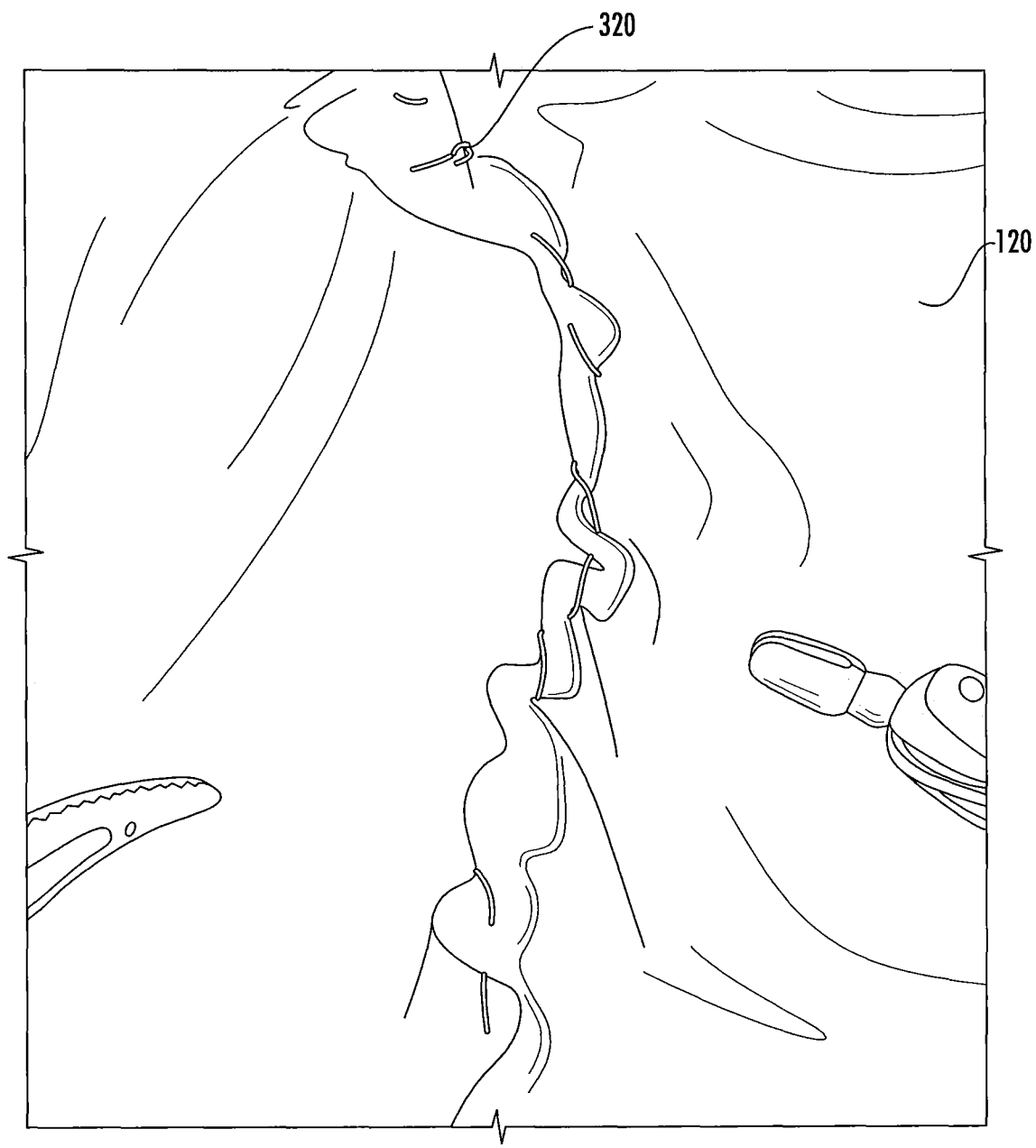
FIG. 17 is a top perspective view from a robotic camera of the surgical training model shown in FIG. 1 in use.

The final step of the simulated sacrocolpopexy surgery using the surgical training model 10 of the present invention is closure of the simulated peritoneum 120 using sutures 320. This is illustrated in FIGS. 16A and 16B. FIG. 17 illustrates the completed closure of the simulated peritoneum 120 over the mesh 300.

As discussed, in some embodiments, the surgical training model 10 may be used to perform a simulated sacrocolpopexy. The method of performing a simulated sacrocolpopexy using the training model 10 of the present invention may include the following steps: (1) providing a surgical training model, the surgical training model comprising a pelvis model that emulates a human pelvis, the pelvis model comprising a simulated skeletal pelvis, a simulated anterior longitudinal ligament, a simulated middle sacral artery, a simulated aorta, a simulated common iliac artery, a simulated internal iliac artery, a simulated external iliac artery, a simulated common iliac vein, a simulated ureter, simulated connective tissue, a simulated peritoneum, and a simulated vagina; (2) positioning the surgical training model within an abdominal wall model, the abdominal wall model optionally comprising apertures defined therein that are configured to receive a laparo scope and/or instrumentation associated with robotic and/or laparoscopic surgery; (3) optionally receiving the laparoscope and/or instrumentation associated with robotic and/or laparoscopic surgery in the abdominal wall model through the apertures (and possibly performing the procedure via an open technique without robotic or laparoscopic instrumentation); (4) dissecting the simulated peritoneum and simulated connective tissue; (5) attaching a mesh to an anterior wall of the simulated vagina; (6) attaching the mesh to a posterior wall of the simulated vagina; (7) attaching the mesh to the simulated anterior longitudinal ligament; and (8) suturing closed the simulated peritoneum over the mesh.

In some embodiments, the surgical training model 10 may be used to perform a simulated Burch urethropexy procedure, a surgical procedure where support is provided to the urethra. The method of performing a simulated Burch urethropexy surgery using the surgical training model 10 of the present invention may include the following steps: (1) providing the surgical training model 10, the surgical training model 10 having a pelvis model that emulates a human pelvis, the pelvis model may include a simulated skeletal pelvis, a simulated Cooper's Ligament, a simulated obturator neurovascular bundle and obturator canal, a simulated obturator internus muscle, a simulated external iliac artery and vein, simulated connective tissue, a simulated peritoneum, a simulated median umbilical ligament, a simulated medial umbilical ligament, a simulated bladder with a simulated urethra, and a simulated vagina; (2) positioning the surgical training model within an abdominal wall model, the abdominal wall model optionally comprising apertures defined therein that are configured to receive a laparoscope and/or instrumentation associated with robotic and/or laparoscopic surgery; (3) optionally receiving the laparoscope and/or instrumentation associated with robotic and/or laparoscopic surgery in the abdominal wall model through the apertures; (4) placing a catheter into the simulated bladder; (5) identifying proper incision line in the simulated peritoneum by retrograde filling the simulated bladder; (6) dissecting the simulated peritoneum; (7) dissecting through the simulated connective tissue; (8) deflating the simulated bladder via the catheter; (9) dissecting and exposing the simulated Cooper's Ligament; (10) placing a distal suture into the simulated vagina and securing to the simulated Cooper's Ligament; (11) placing a proximal suture into the simulated vagina; (12) tying down the distal and proximal sutures; and (13) suturing closed the simulated peritoneum.

In some embodiments, the surgical training model 10 may be used to perform a simulated ureteral reimplantation procedure, a surgical procedure to fix the tubes that connect the bladder to the kidneys. Specific types of ureteral reimplantation procedures that may be simulated using the surgical training model 10 of the present invention may include, but are not limited to, ureteroneocystostomy, Psoas Hitch, Boari flap, and ureteroureterostomy.

For example, in some embodiments, the surgical training model 10 may be used to perform a simulated ureteroneocystostomy, a surgical procedure to reimplant the ureter into the bladder. The method of performing a simulated ureteroneocystostomy procedure using the surgical training model 10 of the present invention may include the following steps: (1) providing the surgical training model 10, the surgical training model 10 having a pelvis model 12 that emulates a human pelvis, the pelvis model 12 may include a simulated skeletal pelvis, a simulated Cooper's Ligament, a simulated obturator neurovascular bundle and obturator canal, a simulated external iliac artery and vein, simulated connective tissue, a simulated peritoneum, a simulated median umbilical ligament, a simulated medial umbilical ligament, a simulated bladder with a simulated urethra, a simulated vagina, a simulated Psoas muscle, a simulated ureter, a simulated Psoas minor tendon, a simulated femoral nerve, and a simulated genitofemoral nerve; (2) positioning the surgical training model within an abdominal wall model, the abdominal wall model optionally comprising apertures defined therein that are configured to receive a laparoscope and/or instrumentation associated with robotic and/or laparoscopic surgery; (3) optionally receiving the laparoscope and/or instrumentation associated with robotic and/or laparoscopic surgery in the abdominal wall model through the apertures; (4) identifying the simulated ureter; (5) dissecting the simulated peritoneum; (6) exposing and mobilizing the simulated ureter; (7) ligating and releasing the distal ureteral segment of the simulated ureter; (8) spatulating the proximal ureteral segment of the simulated ureter; (9) creating a cystotomy on the simulated bladder and placing a stent; and (10) suturing the simulated ureter to the simulated bladder around the stent.

While a surgeon is performing a simulated ureteroneocystostomy surgery using the surgical training model 10 of the present invention, the simulated ureter may not be long enough to reach the simulated bladder without tension. In these situations, the surgical training model 10 allows the surgeon to perform a simulated Psoas hitch procedure. In this simulated procedure, prior to the step of spatulating the proximal ureteral segment of the simulated ureter, the simulated ureteroneocystostomy surgery may include the additional steps of: (1) dissecting the simulated peritoneum and mobilizing the simulated bladder on ipsilateral and contralateral sides; (2) distending the simulated bladder to identify proper site for cystotomy; and (3) anchoring the simulated bladder to the simulated Psoas minor tendon.

If, during the simulated Psoas hitch procedure, the simulated ureter is not long enough to reach the simulated bladder with a Psoas hitch, the surgical training model 10 allows the surgeon to simulate the creation of a Boari flap. In this simulated procedure, after the step of dissecting the simulated peritoneum and mobilizing the simulated bladder on ipsilateral and contralateral sides, the simulated ureteroneocystostomy surgery may further include the steps of: (1) distending the simulated bladder to identify proper site for bladder flap; (2) creating a bladder flap in a rectangular shape on the simulated bladder; (3) suturing the bladder flap to the simulated Psoas tendon; and (4) tubularizing the bladder flap.

In some embodiments, the surgical training model 10 may be used to perform a simulated ureteroureterostomy, a surgical procedure to connect two portions of a transected ureter. The method of performing a simulated ureteroureterostomy procedure using the surgical training model 10 of the present invention may include the following steps: (1) providing a surgical training model 10, the surgical training model 10 having a pelvis model 12 that emulates a human pelvis, the pelvis model 12 may include a simulated skeletal pelvis, a simulated Cooper's Ligament, a simulated obturator neurovascular bundle and obturator canal, a simulated external iliac artery and vein, simulated connective tissue, a simulated peritoneum, a simulated median umbilical ligament, a simulated medial umbilical ligament, a simulated bladder with a simulated urethra, a simulated vagina, a simulated Psoas muscle, a simulated ureter, a simulated Psoas minor tendon, a simulated femoral nerve, and a simulated genitofemoral nerve; (2) positioning the surgical training model within an abdominal wall model, the abdominal wall model optionally comprising apertures defined therein that are configured to receive a laparoscope and/or instrumentation associated with robotic and/or laparoscopic surgery; (3) optionally receiving the laparoscope and/or instrumentation associated with robotic and/or laparoscopic surgery in the abdominal wall model through the apertures; (4) identifying the simulated ureter; (5) dissecting the simulated peritoneum; (6) exposing and mobilizing the simulated ureter; (7) identify injury to the simulated ureter; (8) resecting the edges of the distal and proximal ureteral segments of the simulated ureter; (9) spatulating both the distal and proximal ends of the simulated ureter; and (10) suturing the ureteral anastomosis of the simulated ureter.

In some embodiments, the surgical training model 10 may be used to perform a simulated myomectomy, a surgical procedure to remove uterine leiomyomas (or fibroids). The method of performing a simulated myomectomy using the surgical training model 10 of the present invention may include the following steps: (1) providing a surgical training model, the surgical training model comprising a pelvis model that emulates a human pelvis, the pelvis model comprising a simulated skeletal pelvis, a simulated uterine serosa, a simulated myometrium, a simulated uterus, a simulated myoma, a simulated myoma capsule, and a simulated vagina; (2) positioning the surgical training model within an abdominal wall model, the abdominal wall model optionally comprising apertures defined therein that are configured to receive a laparoscope and/or instrumentation associated with robotic and/or laparoscopic surgery; (3) optionally receiving the laparoscope and/or instrumentation associated with robotic and/or laparoscopic surgery in the abdominal wall model through the apertures; (4) creating an incision through the simulated uterine serosa overlying the simulated myoma; (5) dissecting through the simulated myometrium to the level of the simulated myoma capsule; (6) grasping the simulated myoma with a single-tooth tenaculum; (7) shelling out the simulated myoma from the simulated uterus using a combination of sharp and blunt dissection; and (8) suturing closed the defect in the simulated uterus.

Each of the above described simulated surgical procedures may be performed on the surgical training model 10 of the present invention using robotic, laparoscopic, and/or abdominal/open approach techniques.

EXAMPLES

The following EXAMPLES provide illustrative embodiments. Certain aspects of the following EXAMPLES are disclosed in terms of techniques and procedures found or contemplated by the present inventors to work well in the practice of the embodiments. In light of the present disclosure and the general level of skill in the art, those of skill will appreciate that the following EXAMPLES are intended to be exemplary only and that numerous changes, modifications, and alterations can be employed without departing from the scope of the present invention.

Example 1: Robotic Sacrocolpopexy Simulation Model and Associated Hierarchical Task Analysis Method.

The inventors conducted a two-phase, observational, Carolinas HealthCare System institutional review board exempt simulation study using a dry lab model (IRB File #02-18-27EX). Phase 1 included the model's creation; phase 2 was dedicated to hierarchical task analysis (HTA) development and model assessment.

The pelvic model was constructed to simulate the important structures encountered during pelvic surgery for the purposes of presacral dissection and mesh fixation portions of RSCP. First, a Sawbones® male bony pelvis model, including L4 and L5 vertebrae, sacrum, and coccyx was obtained (www.sawbones.com). A male bony pelvis was used because a narrow pubic arch was optimal to secure the vaginal cuff in place. The anterior longitudinal ligament was created by placing a piece of 2-inch silk tape over the sacrum (see, e.g., FIG. 3). The aorta, common iliac arteries, left common iliac vein, middle sacral artery, and right ureter were sculpted using modeling clay and casted to create reusable molds. Each anatomical structure was created by pouring silicone rubber (Smooth-On Ecoflex™ 0020 and/or 0030) into the molds. Once sculpted, these structures were placed onto the bony pelvis. The vaginal cuff was created with silicone rubber (Smooth-On Ecoflex™ 0030) in the shape of a hollow cylinder. Prior to the RSCP simulation, the cuff was finalized by closing one end with a running suture and then it was secured by wedging the other end in the pubic arch (see, e.g., FIG. 4A). Quilt batting was placed over the vasculature and ureter and under the peritoneum to simulate the areolar tissue (see, e.g., FIG. 5A). Next, the peritoneum was created (Smooth-On Ecoflex™ 0030) and secured to the bony pelvis with binder clips (see, e.g., FIG. 1). The completed model was placed into the Robotic Exercise Kit Abdominal Tunnel and Base (Institute for Surgical Excellence; see, e.g., FIG. 8A) for assessment.

Figure 18A:
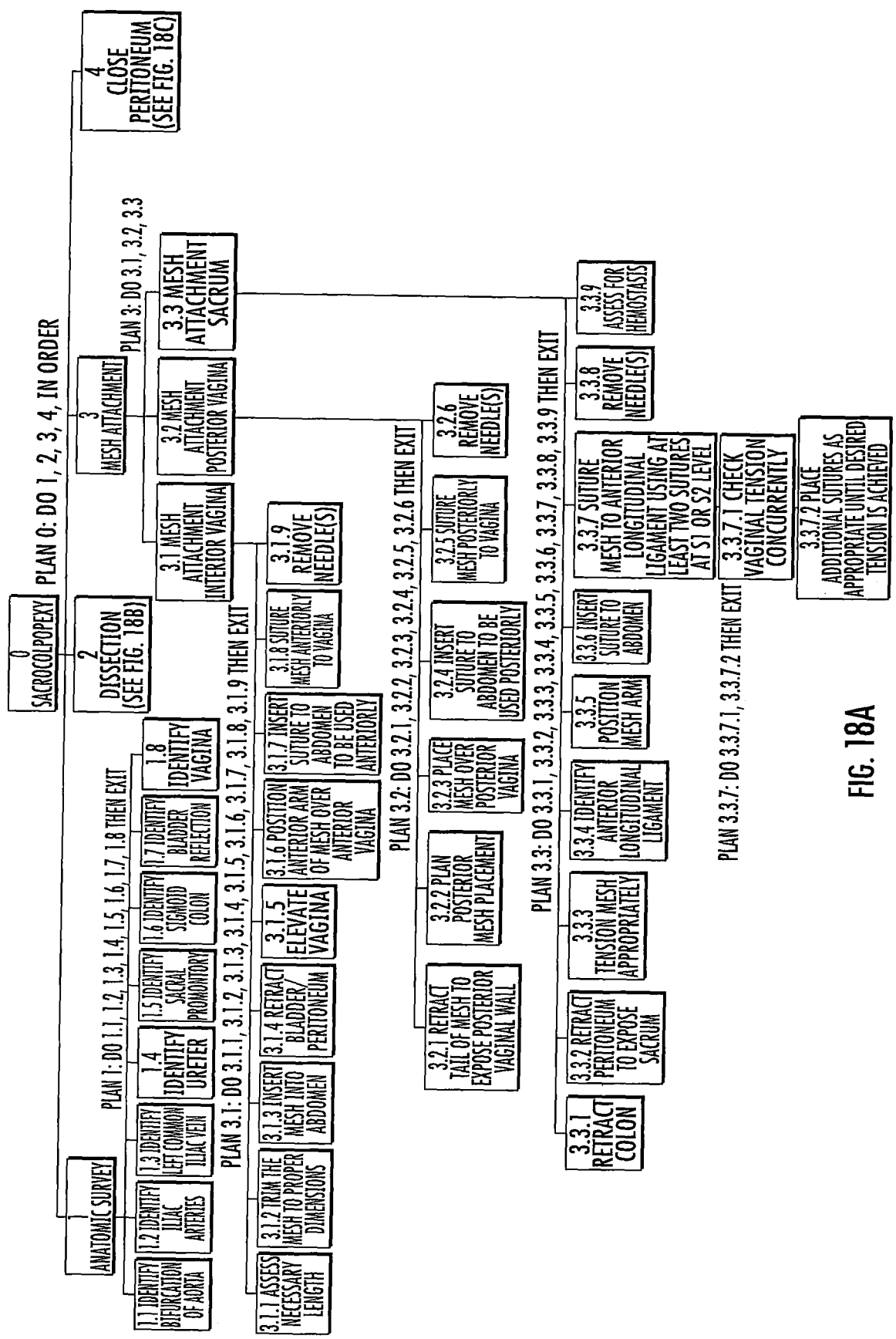
FIGS. 18A-18C are flow diagrams defining tasks and subtasks for a sacrocolpopexy procedure using the surgical training model of FIGS. 1-7B.
Figure 18B:
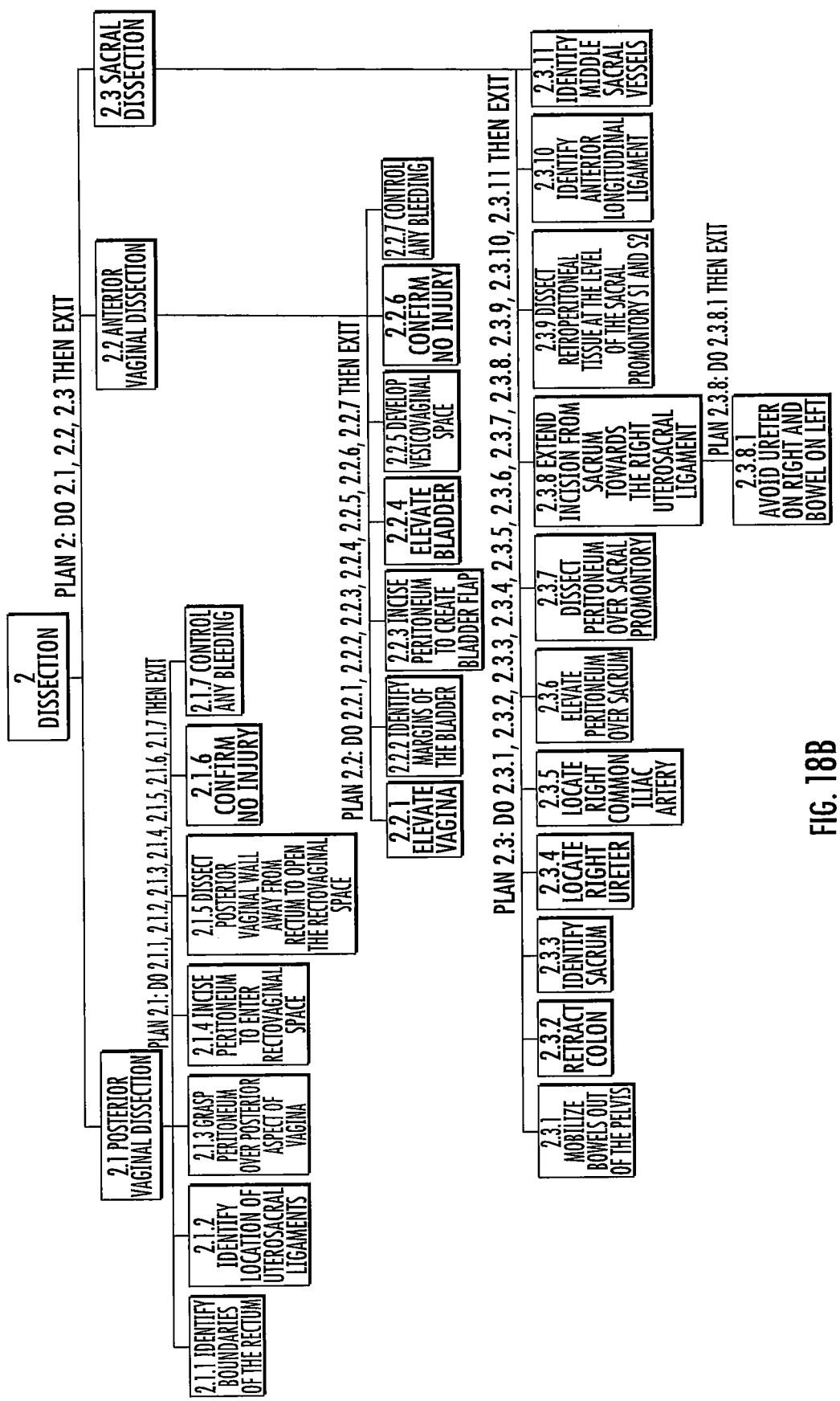
Figure 18C:
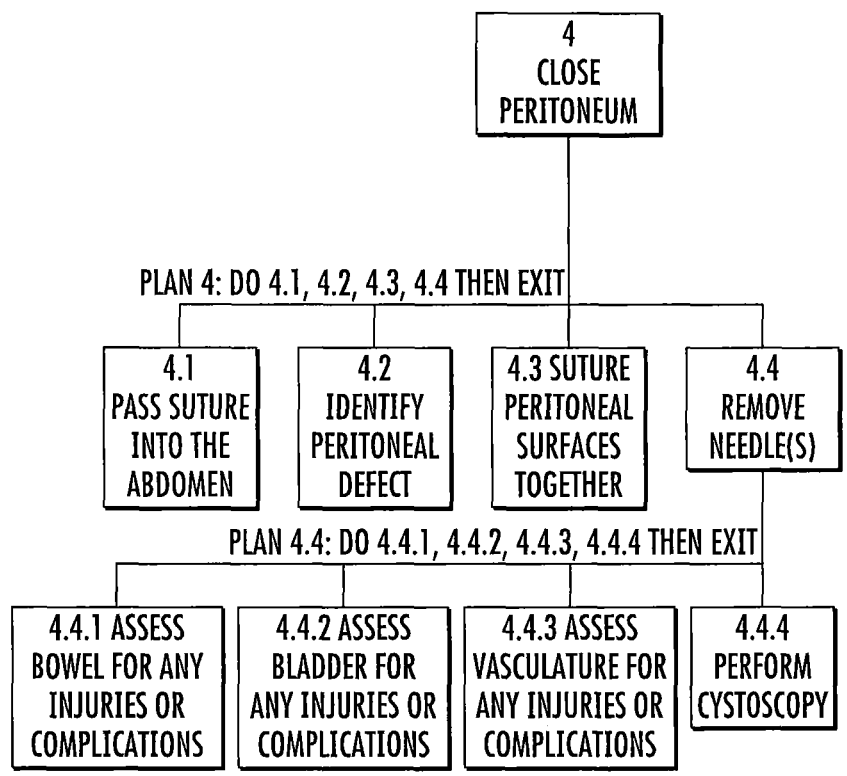

Phase 2 comprised the HTA development and subsequent assessment of the model. Four fellowship-trained female pelvic medicine and reconstructive surgeons who regularly perform minimally invasive RSCP were asked to individually identify and outline each task and subtask of a RSCP. The outline began with trocar placement and concluded with peritoneal closure. Two of the experts were instrumental in development of the model; however, to avoid potential biases, neither was involved in data analysis. A human factors expert compiled the individual procedure outlines into one document with any discrepancies highlighted. The human factors expert then led a session with the four expert surgeons to reach a final consensus, with four major tasks and multiple subtasks identified (FIGS. 18A-18C). A final HTA was then created which was incorporated into a post-procedure questionnaire to evaluate the ability of the model to replicate the expert defined tasks and subtasks. To present the results, the boxes were color coded to represent the responses from the surgeons who participated in the model assessment portion of the study.

Experience.

Participants were recruited using a convenience sample. Experts were defined as fellowship-trained female pelvic medicine and reconstructive surgery (FPMRS) specialists skilled in RSCP who regularly perform this surgery (>100 total procedures performed). Participants were asked to complete two questionnaires and to perform a RSCP using the model. The initial questionnaire obtained demographic information. The post-procedure questionnaire included the HTA checklist to assess if each designated task and subtask of the RSCP could be replicated using the model.

Six FPMRS specialists (2 males, 4 females; mean age 43.3±4.68 years) averaging 40.75±32.84 RSCP procedures per year participated in the study. The HTA confirmed the model was able to replicate most of the steps for presacral dissection and vaginal and presacral mesh attachment, but the model was not able to replicate anterior and posterior vaginal dissection steps (FIGS. 18A-18C).

Discussion.

According to the HTA, the presented model allows for replicating the steps of presacral dissection with vaginal/sacral mesh attachment at the time of RSCP. Additionally, the model replicates the steps necessary for presacral dissection and sacral mesh attachment at the time of RSCP. This study is unique as the six experts who assessed the model were not involved in the creation of the model and they practice at five different medical institutions across the United States. Additionally, the use of the HTA methodology allows for a systematic way for experts to assess the model's ability to replicate predefined procedural steps.

Previous resources for robotic surgeons in training were limited to robotic simulation drills. The first one described at University of Texas South Western included a proficiency based robotic curriculum based on inanimate tasks with proven construct, content, and face validity. Likewise, the Robotic Training Network curriculum was a multicenter validated robotic training curriculum with construct validity and proven inter/intra-rater reliability for training tasks such as tower transfer, roller coaster, big dipper needle manipulation, train tracks needle manipulation, and figure of eight suturing/knot tying. Since these dry lab curricula have been described, virtual reality robotic simulation drills have been developed and correlate to the Robotic Training Network dry lab skills.

The model of the present invention fills a need for procedural based robotic simulation for complex surgical tasks as it allows surgeons to practice procedure specific skills after they have mastered the training tasks and drills listed above. The procedural-specific HTA developed by the human factors expert and expert surgeons skilled in RSCP offers an objective method to evaluate the model's ability to replicate necessary steps of the RSCP procedure. Subsequent validation studies are necessary to better understand the ability of the model of the present invention to be used by robotic surgeons in training and perhaps even for maintenance of skills.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A surgical training model for use in performing simulated sacrocolpopexy surgery using robotic or laparoscopic techniques, the surgical training model comprising a pelvis model that emulates a human pelvis, the pelvis model consisting of a skeletal pelvis, an anterior longitudinal ligament, a middle sacral artery, an aorta, a common iliac artery, an internal iliac artery, an external iliac artery, a vena cava, a common iliac vein, a ureter, connective tissue, a peritoneum, and a vagina,
wherein the model is configured for use with a robotic or laparoscopic surgical system.

2. The surgical training model of claim 1, wherein the pelvis model further comprises sacral nerve roots, uterosacral ligaments, a bladder, a rectum, a uterus, ovaries, and fallopian tubes.

3. The surgical training model of claim 1, wherein the skeletal pelvis model includes an ilium, an ischium, a pubis, a sacrum having sacral promontory, and a coccyx.

4. The surgical training model of claim 1, wherein the pelvis model is a 3D-printed model.

5. The surgical training model of claim 1, wherein an abdominal wall model overlays the pelvis model.

6. The surgical training model of claim 5, wherein the abdominal wall model comprises apertures defined therein that are configured to receive a laparoscope and/or instrumentation associated with laparoscopic surgery.

7. The surgical training model of claim 5, wherein the abdominal wall model comprises apertures defined therein that are configured to receive robotic instrumentation associated with robotic surgery.

8. The surgical training model of claim 5, wherein the abdominal wall model is configured to simulate an abdominal/open approach surgery.

9. The surgical training model of claim 1, wherein the anterior longitudinal ligament, the middle sacral artery, the aorta, the common iliac artery, the internal iliac artery, the external iliac artery, the common iliac vein, the ureter, the connective tissue, the peritoneum, and the vagina are releasably attached to the pelvis model via an adhesive or a hook and loop fastener.

10. The surgical training model of claim 1, wherein the skeletal pelvis, the anterior longitudinal ligament, the middle sacral artery, the aorta, the common iliac artery, the internal iliac artery, the external iliac artery, the common iliac vein, and/or the ureter are reusable.

11. The surgical training model of claim 1, wherein the loose connective tissue covers the middle sacral artery, the right and left common iliac arteries, the internal and external iliac arteries, the left common iliac vein, the aorta, and the ureter, and is received underneath the vagina.

12. The surgical training model of claim 11, wherein the peritoneum covers the loose connective tissue and is received underneath the vagina.

13. The surgical training model of claim 1, wherein the peritoneum is adhered or otherwise attached to an outer periphery or an outer peripheral portion of the pelvis model.

14. A method of performing a simulated sacrocolpopexy surgery using robotic or laparoscopic, the method comprising:
providing a surgical training model, the surgical training model comprising a pelvis model that emulates a human pelvis, the pelvis model consisting of a simulated skeletal pelvis, a simulated anterior longitudinal ligament, a simulated middle sacral artery, a simulated aorta, a simulated common iliac artery, a simulated internal iliac artery, a simulated external iliac artery, a simulated common iliac vein, a simulated ureter, simulated connective tissue, a simulated peritoneum, and a simulated vagina, wherein the simulated anterior longitudinal ligament, the simulated middle sacral artery, the simulated aorta, the simulated common iliac artery, the simulated internal iliac artery, the simulated external iliac artery, the simulated common iliac vein, the simulated ureter, the simulated connective tissue, the simulated peritoneum, and the simulated vagina are each individually releasably attached to the pelvis model;
positioning the surgical training model within an abdominal wall model, wherein the abdominal wall model optionally comprises apertures defined therein that are configured to receive a laparoscope and/or instrumentation associated with robotic and/or laparoscopic surgery;
optionally receiving the laparoscope and/or instrumentation associated with robotic and/or laparoscopic surgery in the abdominal wall model through the apertures;
dissecting the simulated peritoneum and simulated connective tissue;
attaching a mesh to an anterior wall of the simulated vagina;
attaching the mesh to a posterior wall of the simulated vagina;

attaching the mesh to the simulated anterior longitudinal ligament; and suturing closed the simulated peritoneum over the mesh.

15. The method of claim 14, wherein the pelvis model further comprises a simulated bladder and a simulated rectum, the method further comprising the step of:

dissecting the simulated bladder and simulated rectum away from the simulated vagina prior to the step of attaching the mesh to the anterior wall of the simulated vagina.

16. A surgical training model for use in performing simulated sacrocolpopexy surgery using robotic or laparoscopic techniques, the surgical training model comprising a pelvis model that emulates a human pelvis, the pelvis model consisting of a skeletal pelvis, an anterior longitudinal ligament, a middle sacral artery, an aorta, a common iliac artery, an internal iliac artery, an external iliac artery, a vena cava, a common iliac vein, a ureter, connective tissue, a peritoneum, and a vagina, wherein the model is configured for use with a robotic or laparoscopic surgical system, and wherein the anterior longitudinal ligament, the middle sacral artery, the aorta, the common iliac artery, the internal iliac artery, the external iliac artery, the common iliac vein, the ureter, the connective tissue, the peritoneum, and the vagina are each individually releasably attached to the pelvis model.

* * * * *